US009801630B2

(12) United States Patent
Harris et al.

(10) Patent No.: US 9,801,630 B2
(45) Date of Patent: Oct. 31, 2017

(54) METHODS AND DEVICES FOR REINFORCING A STAPLE LINE

(71) Applicant: Ethicon LLC, Guaynabo, PR (US)

(72) Inventors: Jason L. Harris, Lebanon, OH (US); Frederick E. Shelton, IV, Hillsboro, OH (US); Suzanne E. Thompson, West Chester, OH (US); Dennis D. Jamiolkowski, Long Valley, NJ (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 473 days.

(21) Appl. No.: 14/300,801

(22) Filed: Jun. 10, 2014

(65) Prior Publication Data

US 2015/0351757 A1 Dec. 10, 2015

(51) Int. Cl.

| | |
|---|---|
| ***A61B 17/072*** | (2006.01) |
| *A61B 17/068* | (2006.01) |
| *A61B 17/00* | (2006.01) |

(52) U.S. Cl.

CPC ...... *A61B 17/07292* (2013.01); *A61B 17/072* (2013.01); *A61B 17/068* (2013.01);

(Continued)

(58) Field of Classification Search

CPC . A61B 17/068; A61B 17/0686; A61B 17/072; A61B 17/07207; A61B 17/07292;

(Continued)

(56) References Cited

U.S. PATENT DOCUMENTS

| | | |
|---|---|---|
| 5,698,213 A | 12/1997 | Jamiolkowski et al. |
| 5,700,583 A | 12/1997 | Jamiolkowski et al. |

(Continued)

FOREIGN PATENT DOCUMENTS

| | | |
|---|---|---|
| EP | 2870937 A1 | 5/2015 |
| WO | 2014016819 A1 | 1/2014 |

OTHER PUBLICATIONS

Chen et al. "Elastomeric Biomaterials for Tissue Engineering." Prog. Polymer. Sci. 38(2013):584-671.

(Continued)

*Primary Examiner* — Scott A. Smith

(74) *Attorney, Agent, or Firm* — Mintz Levin Cohn Ferris Glovsky and Popeo, P.C.

(57) ABSTRACT

Adjunct material and methods of using adjunct material to reinforce tissue in proximity to a staple line are provided herein. In general, the adjunct material can be used to maintain a seal in tissue, such as lung tissue, and prevent stapled tissue from tearing. This adjunct material can be coupled to a jaw of a surgical stapler, and can be deployed into tissue along with the staples. In some embodiments, the adjunct material can comprise an outer material encompassing an inner, hydrophilic swellable material. The outer material can be selectively dissolvable and/or absorbable. When the outer material is punctured by staples or otherwise penetrated, moisture is passed to the inner material which then swells and expands to transition to a predetermined shape to seal the tissue and prevent leaks from forming in the tissue. Portions of the inner material around the staple line can transition to a large radius.

16 Claims, 20 Drawing Sheets

(52) U.S. Cl.
CPC .................... *A61B 17/07207* (2013.01); *A61B 2017/00004* (2013.01); *A61B 2017/00336* (2013.01); *A61B 2017/00898* (2013.01); *A61B 2017/00942* (2013.01); *A61B 2017/00964* (2013.01); *A61B 2017/07242* (2013.01)

(58) Field of Classification Search
CPC .............. A61B 17/115; A61B 17/1155; A61B 2017/07214; A61B 2017/00884; A61B 2017/00893
USPC .......... 227/19, 175.1, 176.1, 180.1; 606/139, 606/143, 151, 215, 219
See application file for complete search history.

(56) References Cited

U.S. PATENT DOCUMENTS 6,605,294 B2 * 8/2003 Sawhney ......... A61B 17/12022 424/426
7,143,924 B2 12/2006 Scirica et al.
7,143,925 B2 12/2006 Shelton, IV et al.
7,438,209 B1 * 10/2008 Hess .................. A61B 17/0643 227/176.1
7,735,703 B2 * 6/2010 Morgan ............... A61B 17/105 227/176.1
7,772,352 B2 8/2010 Bezwada
8,317,070 B2 11/2012 Hueil et al.
8,393,514 B2 3/2013 Shelton, IV et al.
8,551,058 B2 10/2013 Measamer et al.
2005/0059996 A1 * 3/2005 Bauman ............... A61B 17/072 606/215
2006/0085030 A1 4/2006 Bettuchi et al.
2006/0173470 A1 * 8/2006 Oray ................ A61B 17/07207 606/151
2006/0257458 A1 11/2006 Gorman et al.
2006/0271104 A1 11/2006 Viola et al.
2007/0243227 A1 * 10/2007 Gertner ................ A61B 17/068 424/424
2008/0110961 A1 * 5/2008 Voegele ............. A61B 17/0644 227/179.1
2008/0140115 A1 * 6/2008 Stopek ................. A61B 17/068 606/219
2008/0161831 A1 * 7/2008 Bauman ............... A61B 17/072 606/148
2008/0188766 A1 * 8/2008 Gertner ................. A61F 5/0086 600/561
2009/0234193 A1 9/2009 Weisenburgh, II et al.
2009/0270686 A1 10/2009 Duke et al.
2010/0331880 A1 * 12/2010 Stopek ............... A61B 17/0644 606/219
2011/0192882 A1 8/2011 Hess et al.
2012/0024934 A1 2/2012 Shelton, IV et al.
2012/0080335 A1 4/2012 Shelton, IV et al.
2012/0083835 A1 4/2012 Shelton, IV et al.
2012/0241492 A1 * 9/2012 Shelton, IV ......... A61B 17/068 227/175.1
2012/0241498 A1 9/2012 Gonzalez et al.
2012/0241505 A1 9/2012 Alexander, III et al.
2013/0068820 A1 3/2013 Miller et al.
2013/0112733 A1 5/2013 Aranyi et al.
2013/0123816 A1 * 5/2013 Hodgkinson ........... A61L 31/06 606/151
2013/0146641 A1 6/2013 Shelton, IV et al.
2013/0146642 A1 6/2013 Shelton, IV et al.
2013/0153641 A1 6/2013 Shelton, IV et al.
2013/0161374 A1 6/2013 Swayze et al.
2013/0256365 A1 10/2013 Shelton, IV et al.
2013/0256372 A1 10/2013 Baxter, III et al.
2013/0256376 A1 10/2013 Barton et al.
2013/0256377 A1 10/2013 Schmid et al.
2014/0158741 A1 6/2014 Woodard, Jr. et al.
2015/0173756 A1 6/2015 Baxter, III et al.
2015/0272575 A1 10/2015 Leimbach et al.

OTHER PUBLICATIONS

Lim et al. "Fabrication and Evaluation of Poly(epsilon-caprolactone)/Silk Fibroin Blend Nanofibrous Scaffold." Biopolymers. 97(2012):265-275.
U.S. Appl. No. 13/763,192, filed Feb. 8, 2013.
U.S. Appl. No. 14/074,810, filed Nov. 8, 2013.
U.S. Appl. No. 14/074,884, filed Nov. 8, 2013.
U.S. Appl. No. 14/074,902, filed Nov. 8, 2013.
U.S. Appl. No. 14/075,438, filed Nov. 8, 2013.
U.S. Appl. No. 14/075,459, filed Nov. 8, 2013.
U.S. Appl. No. 14/300,793, filed Jun. 10, 2014.
U.S. Appl. No. 14/300,799, filed Jun. 10, 2014.
U.S. Appl. No. 14/300,804, filed Jun. 10, 2014.
U.S. Appl. No. 14/300,807, filed Jun. 10, 2014.
U.S. Appl. No. 14/300,811, filed Jun. 10, 2014.
U.S. Appl. No. 14/300,815, filed Jun. 10, 2014.
U.S. Appl. No. 14/300,817, filed Jun. 10, 2014.
U.S. Appl. No. 14/300,819, filed Jun. 10, 2014.
U.S. Appl. No. 14/300,820, filed Jun. 10, 2014.
U.S. Appl. No. 14/300,954, filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.
European Search Report for Application No. EP 15171467.2 dated Dec. 22, 2015.
International Search Report and Written Opinion for Application No. PCT/US2015/031667 dated Sep. 23, 2015.

* cited by examiner

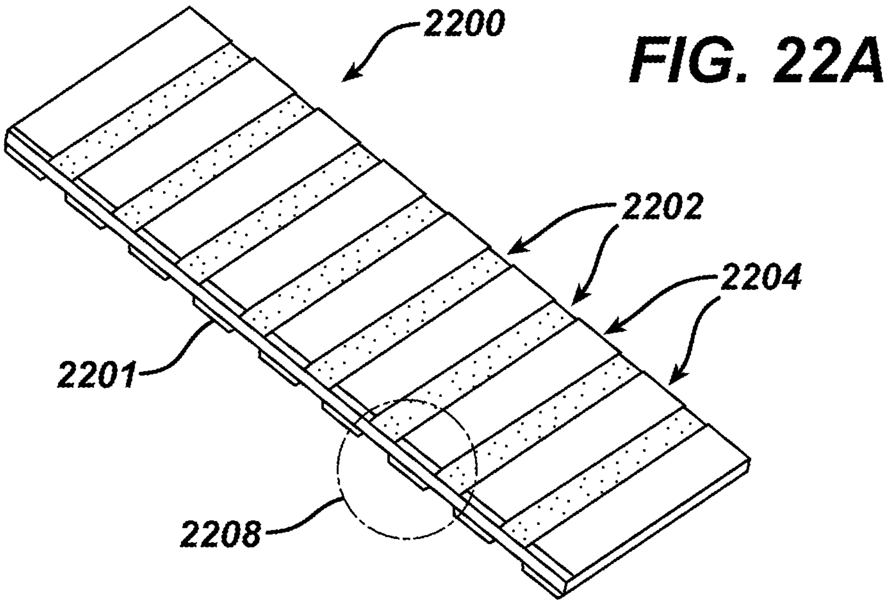
FIG. 22A
FIG. 22B
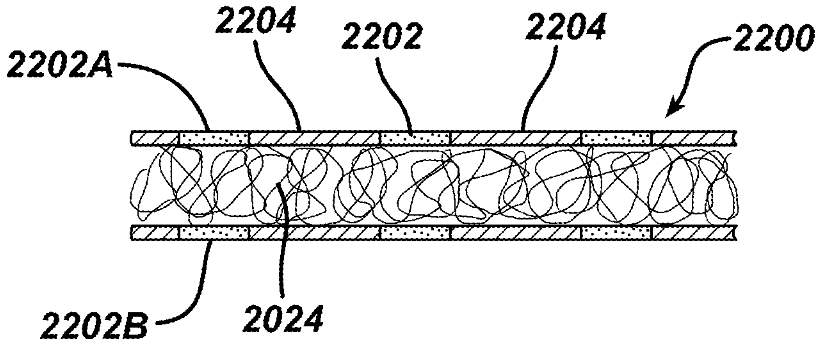

METHODS AND DEVICES FOR REINFORCING A STAPLE LINE

FIELD

The subject matter disclosed herein relates to methods and devices for reinforcing a staple line.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate flexible or rigid shaft having a pair of opposed jaws formed on an end thereof for holding and forming staples therebetween. At least one of the opposed jaws is movable relative to the other jaw. In the case of laparoscopic surgery, often one jaw is fixed and the other is movable. In some devices (for example an open linear stapler), the opposed jaws can be separated by the operator and reassembled providing the relative motion needed for tissue placement. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut the stapled tissue between the stapled rows. Placement of the device, manipulation of components or systems of the device, and other actuations of the device such as articulation, firing, etc. can be accomplished in a variety of ways, such as electromechanically, mechanically, or hydraulically.

While surgical staplers have improved over the years, a number of problems can potentially arise. Although rare, as illustrated in FIG. 1, one problem is that leaks can occur due to staples S forming tears H when penetrating a tissue T or other object in which the staples S are disposed. Blood, air, gastrointestinal fluids, and other fluids can seep through the tears H formed by the staples S, even after the staples S are fully formed. The tissue T being treated can also become inflamed due to the manipulations and deformations that can occur during stapling. Still further, staples, as well as other objects and materials implanted during stapling procedures, generally lack the same characteristics as tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for methods and devices for reinforcing a staple line.

SUMMARY

Some embodiments relate to a staple cartridge assembly for use with a surgical stapler. In one embodiment, the staple cartridge assembly can include a cartridge body having a plurality of staple cavities configured to seat staples therein, and a tissue reinforcement construct removably attached to the cartridge body and configured to be delivered to tissue by deployment of the staples in the cartridge body. The tissue reinforcement construct can include a first, absorbable material encompassing a swellable, hydrophilic second material such that the second material is maintained within the first material in a constrained configuration. The second material can have a preconfigured shape such that, in an unconstrained configuration, the second material is adapted to expand to the preconfigured shape in which a peripheral edge portion of the second material has a thickness that is greater than a central portion of the second material.

The assembly can have any number of variations. For example, at least a portion of the first material can be less hydrophilic than the second material. For another example, the first material can be brittle. For yet another example, the second material can include a foam material. For another example, the first material can be selectively dissolvable such that portions of the first material encompassing the peripheral edge portions of the second material are adapted to dissolve at a faster rate than portions of the first material encompassing the central portion of the second material. For still another example, the first material can include at least one first portion and at least one second portion, and the first material can be selectively dissolvable such that the at least one first portion is adapted to dissolve at a faster rate than the at least one second portion. For another example, the first material can be selectively absorbable such that portions of the first material encompassing the peripheral edge portions of the second material are adapted to absorb at a faster rate than portions of the first material encompassing the central portion of the second material. For yet another example, the first material can include at least one first portion and at least one second portion, and the first material can be selectively absorbable such that the at least one first portion is adapted to absorb at a faster rate than the at least one second portion. For another example, the first material can be selected from the group consisting of polydioxanon, polyhydroxyalkanoate (PHA), polyglycerol sebacate (PGS), polyglycolic acid, polylactic acid (PLA), poliglecaprone 25, polyglactin 910, poly glyconate, polyglycolide (PGA), polyglycolide-trimethylene carbonate (PGA/TMC), polyhydroxybutyrate (PHB), poly(vinylpyrrolidone) (PVP), poly(vinyl alcohol) (PVA), absorbable polyurethanes, a blend thereof, and a copolymer thereof. For still another example, the second material can be selected from the group consisting of polydioxanon, polyhydroxyalkanoate (PHA), Polyglycerol sebacate (PGS), polyglycolic acid, polylactic acid (PLA), poliglecaprone 25, polyglactin 910, poly glyconate, polyglycolide (PGA), polyglycolide-trimethylene carbonate (PGA/TMC), polyhydroxybutyrate (PHB), poly(vinylpyrrolidone) (PVP), poly(vinyl alcohol) (PVA), absorbable polyurethanes, a blend thereof, and a copolymer thereof. For yet another example, the assembly can include at least one therapeutic agent incorporated into at least one of the first material and the second material, and the at least one therapeutic agent can be effective to be released upon one of absorption of the first material and expansion of the second material upon exposure to moisture. For another example, the tissue reinforcement construct can be shaped such that a cross-section of the peripheral edge portion of the tissue reinforcement construct is larger than a cross-section of the central portion of the tissue reinforcement construct, and the central portion can be closer to a longitudinal axis of the tissue reinforcement construct than the peripheral edge portion. The preconfigured shape can be such that the central portion of the second material transitions to a large radius at the peripheral edge.

In another embodiment, a staple cartridge assembly for use with a surgical stapler can include a cartridge body having a plurality of staple cavities configured to seat staples therein, and an adjunct material releasably retained on the cartridge body and configured to be delivered to tissue by deployment of the staples in the cartridge body. The adjunct material can include a first material encompassing a second material. The adjunct material can be configured to be penetrated by the staples being delivered to the tissue such that the first material is penetrated so as to expose the second material to moisture, and the second material can be configured to expand to form a seal around at least one staple of the staples inserted therethrough upon the exposure to moisture.

The first material can be formed from a variety of materials; particularly advantageous are those materials that are absorbable and capable bearing compressive and bending loads. They may be present in continuous form so as to fully encapsulate the materials making up the center of the device, or alternately they might be present in a non-continuous form. These non-continuous forms include, but are not limited to, otherwise encapsulating forms with minute openings allowing water or bodily fluids to access the materials making up the center of the device to facilitate rapid hydration to allow expansion of the center material; melt blend nonwoven forms with controlled porosity; immiscible polymer blends having a major blend component an absorbable polymer and a minor component being a biocompatible water soluble polymer which is capable of rapidly dissolving creating conduits to the central material allowing for its rapid hydration to generate an external force on the tissue.

The absorbable polymer making up the outer layer, although not limited to, can be selected from the group consisting of polydioxanone [AKA poly(1,4-dioxan-2-one), or poly(p-dioxanone)]; polyglycolide [AKA polyglycolic acid], polylactide [AKA polylactic acid] in all its forms based on the ring-opening of the corresponding lactone monomers, L(−)-lactide, D(+)-lactide, and meso-lactide, as well as all of its forms based upon polycondensation of L(+)-lactic acid and D(−)-lactic acid [e.g. poly(L(−)-lactide), poly(D(+)-lactide), poly(meso-lactide), poly(racemic-lactide), poly(L-lactic acid), poly(D-lactic acid), etc.]; the polycaprolactones, especially poly(epsilon-caprolactone); polyhydroxyalkanoate (PHA); the absorbable copolymers usually formed by the ring-opening polymerization of the lactone monomers, L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. These later copolymers include, but are not limited to epsilon-caprolactone/glycolide copolymers such as 25/75 poly(caprolactone-co-glycolide) [AKA poliglecaprone 25], 10/90 poly(L(−)-lacide-co-glycolide) [AKA polyglactin 910], polyglyconate, polyglycolide-trimethylene carbonate (PGA/TMC). The absorbable polymer can be a miscible or immiscible blend of the previously mentioned polymers [and copolymers] in any combination. It will be clear to one skilled in the art to select a biocompatible material.

The second material may be formed from a variety of materials. Advantageous materials include those that are absorbable and can undergo a controlled degree of swelling so as to create an external force on the tissue. Swelling might be accomplished by hydration based on an influx of water or bodily fluids. One class of materials that is particularly advantageous are absorbable dehydrated hydrogels. These include the materials described in U.S. Pat. No. 5,698,213, entitled "Hydrogels of Absorbable Polyoxaesters" and crosslinked aliphatic polyoxaesters containing amine and/or amido groups and blends thereof with other polymers as described in U.S. Pat. No. 5,700,583, each of which is incorporated herein by reference in its entirety. Other materials suitable for the second material include water soluble polymers such as poly(vinylpyrrolidone) (PVP), poly(vinyl alcohol) (PVA), and polyethylene glycol (PEG) or the higher molecular weight polyethylene oxide (PEO). Additionally suitable are absorbable polyurethanes. It is to be understood that suitable materials include copolymers that contain a hydrophilic section and an absorbable polyester section; this would include, by way of example, the copolymer made by reaction of a relatively low molecular weight alpha,omega-dihydroxy polyethylene glycol and a lactone monomer such as L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. Blends of materials and copolymers formed from a wide variety of suitable monomers, some already mentioned above, may be suitable. It will be clear to one skilled in the art to select a biocompatible material.

The assembly can have any number of variations. For example, the adjunct material can be positioned on the cartridge body such that at least a portion of the adjunct material extends beyond the cartridge body.

In another aspect, a method for joining tissue is provided that in one embodiment can include engaging tissue between a cartridge assembly and an anvil of a surgical stapler at a surgical site. At least one of the cartridge assembly and the anvil can have an adjunct material releasably retained thereon. The adjunct material can include a first material, at least a portion of which being configured to dissolve when exposed to bodily fluid, and a second material constrained within the first material in a constrained form. The method can further include actuating the surgical stapler to eject staples from the cartridge into the tissue such that at least one staple from the staples extends through the adjunct material to maintain the material at the surgical site. The second material can be configured to transition to a predetermined shape upon dissolution of the first material such that at least a peripheral edge portion of the adjunct material has a thickness greater than a central portion of the adjunct material. The method can have any number of variations.

BRIEF DESCRIPTION OF THE DRAWINGS

The invention will be more fully understood from the following detailed description taken in conjunction with the accompanying drawings, in which:

FIG. 22A is a perspective view of the adjunct material including portions of an outer material having different characteristics, in accordance with some embodiments;

FIG. 22B is a side view of the adjunct material of FIG. 22A, in accordance with some embodiments;

DETAILED DESCRIPTION

Figure 1:
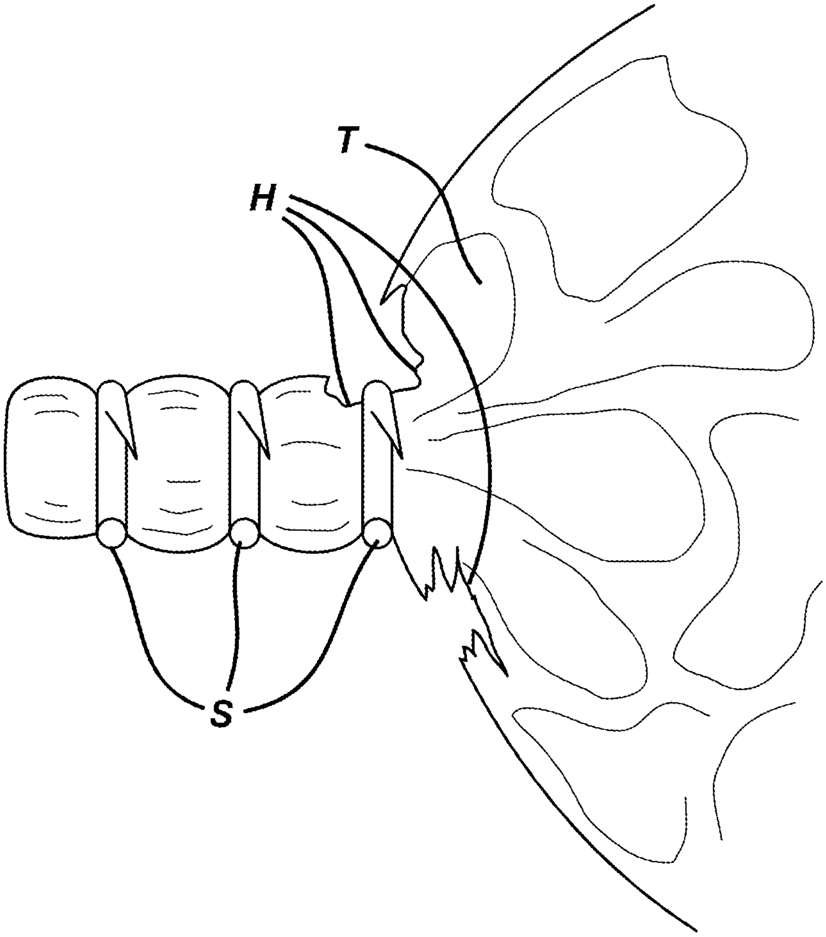
FIG. 1 is a side view of damaged stapled tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

It can be desirable to use one or more biologic materials and/or synthetic materials, collectively referred to herein as "adjunct materials," in conjunction with surgical instruments to help improve surgical procedures. These biologic materials may be derived from human and/or animal sources. A person skilled in the art may refer to these types of materials as buttress materials as well as adjunct materials.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

End effectors of the surgical instruments as described herein can be configured to deliver one or more synthetic materials and/or biologic materials, collectively referred to herein as "adjunct materials," to a surgical site to help improve surgical procedures. These biologic materials may be derived from human and/or animal sources. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the adjunct material(s) can be used to help seal holes formed by staples as they are implanted into tissue, blood vessels, and various other objects or body parts, and/or can be used to provide tissue reinforcement at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct material(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct material(s) can be configured to wick or absorb beneficial fluids, e.g., sealants, blood, glues, that further promote healing, and in some instances, the adjunct material(s) can be configured to degrade to form a gel, e.g., a sealant, that further promotes healing. In some instances, the adjunct may carry materials that when placed into a wet environment (e.g., blood, water, saline, or other bodily fluids) form a sealant to create a seal (e.g., human or animal derived fibrinogen and thrombin can be lyophilized into a powder form that when mixed with water creates a sealant). Still further, the material(s) can help reduce inflammation, promote cell growth, and otherwise improve healing.

Figure 2:
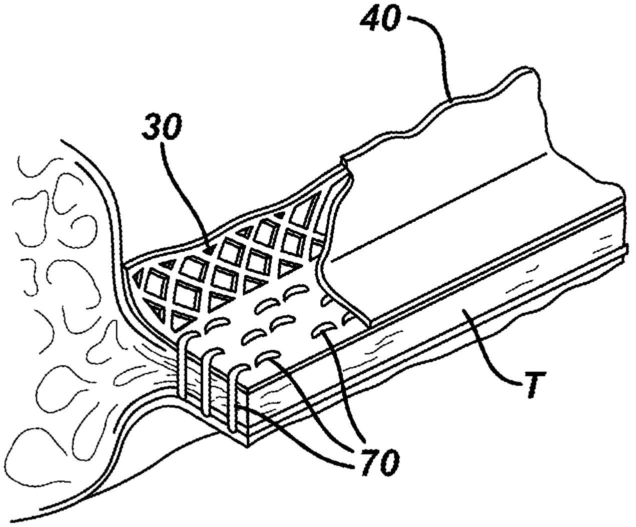
FIG. 2 is a perspective view of one embodiment of an adjunct material as described herein that is fixed to stapled tissue.

FIG. 2 illustrates one embodiment of an adjunct material that includes a porous buttress 30 that can be fixed to a tissue T to be treated by a surgical stapler and that remains at the treatment site with staples 70. The buttress 30 can be made from one or more absorbent materials and can be stamped, pressed, cut, molded, woven, melted, blown, comprised from composite structures and/or methods or otherwise shaped to facilitate absorption, reinforcement, delivery and/or retention of beneficial fluids such as sealants, glues, blood, etc. The absorption and/or retention of beneficial fluids, for example a fibrin sealant 40, at the treatment site can further help to prevent leaks and to reinforce the buttress 30.

Surgical Stapling Instrument

Figure 3:
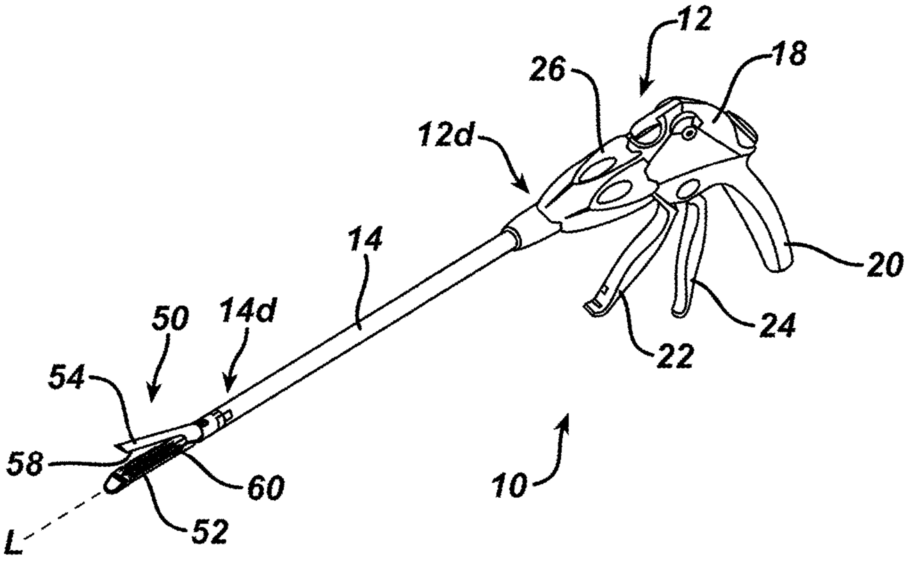
FIG. 3 is a perspective view of a prior art surgical instrument which can be used with one or more adjunct materials.

While a variety of surgical instruments can be used in conjunction with the adjunct materials disclosed herein, FIG. 3 illustrates one, non-limiting exemplary embodiment of a surgical stapler 10 suitable for use with one or more adjunct materials. The instrument 10 generally includes a handle assembly 12, a shaft 14 extending distally from a distal end **12*d* of the handle assembly 12, and an end effector 50 at a distal end 14*d* of the shaft 14. Because the illustrated embodiment is a surgical stapler, the end effector 50 has jaws 52, 54, although other types of end effectors can be used with the shaft 14, handle assembly 12, and components associated with the same. The surgical stapler 10 includes opposed lower and upper jaws 52, 54 with the lower jaw 52 including a staple channel 56 (FIG. 4) configured to support a staple cartridge 60, and the upper jaw 54 having an inner surface 58 that faces the lower jaw 52 and that is configured to operate as an anvil to help deploy staples 70 of the staple cartridge 60. The jaws 52, 54 are configured to move relative to one another to clamp tissue or other objects disposed therebetween, and components of a firing system can be configured to pass through at least a portion of the end effector 50 to eject the staples into the clamped tissue. In various embodiments a knife blade 81 can be associated with the firing system to cut tissue during the stapling procedure. At least one of the opposed lower and upper jaws 52, 54 will be moveable relative to the other lower and upper jaws 52, 54. At least one of the opposed lower and upper jaws 52, 54 may be fixed or otherwise immovable. In some embodiments, both of the opposed lower and upper jaws 52, 54** will be movable.

Operation of the end effector 50 can begin with input from a clinician at the handle assembly 12. The handle assembly 12 can have many different configurations designed to manipulate and operate the end effector 50 associated therewith. In the illustrated embodiment, the handle assembly 12 has a pistol-grip type housing 18 with a variety of mechanical and/or electrical components disposed therein to operate various features of the instrument. For example, the handle assembly 12 can include a rotation knob 26 mounted adjacent a distal end **12*d* thereof which can facilitate rotation of the shaft 14 and/or the end effector 50 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 52, 54 to collapse towards each other and to thereby clamp tissue therebetween. Movement of the firing trigger 24 can actuate the firing system, described below, which can cause the ejection of staples from a staple cartridge disposed therein and/or the advancement the knife blade 81 to sever tissue captured between the jaws 52, 54**. A person skilled in the art will recognize that various configurations of components for a firing system, mechanical, hydraulic, pneumatic, electromechanical, robotic, or otherwise, can be used to eject staples and/or cut tissue, and thus a detailed explanation of the same is unnecessary.

Figure 4:
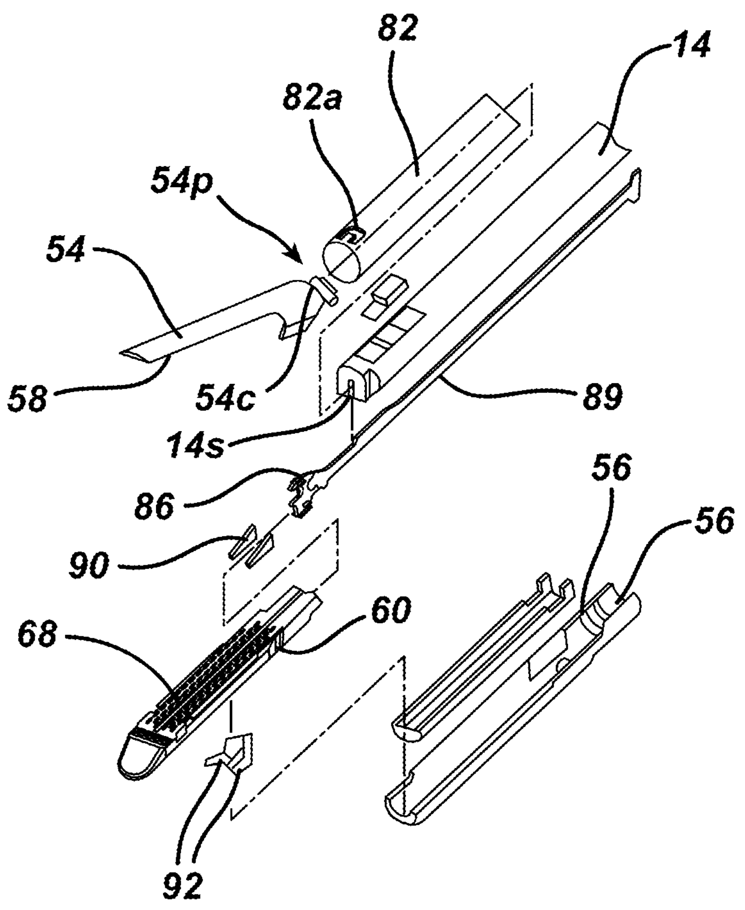
FIG. 4 is an exploded perspective view of an end effector and a distal end of a shaft of the instrument of FIG. 3.

As shown in more detail in FIG. 4, the end effector 50 of the illustrated embodiment is a surgical stapling tool having a lower jaw 52 that serves as a cartridge assembly or carrier and an opposed upper jaw 54 that serves as an anvil. The staple cartridge 60, having a plurality of staples 70 therein, is supported in a staple tray 57, which in turn is supported within the cartridge channel of the lower jaw 52. The upper jaw 54 has a plurality of staple forming pockets 66 (FIG. 11), each of which is positioned above a corresponding staple from the plurality of staples 70 contained within the staple cartridge 60. The upper jaw 54 can be connected to the lower jaw 52 in a variety of ways, although in the illustrated embodiment the upper jaw 54 has a proximal pivoting end 54*p* that is pivotally received within a proximal end 56*p* of the staple channel 56, just distal to its engagement to the shaft 14. When the upper jaw 54 is pivoted downwardly, the upper jaw 54 moves the anvil surface 58 and the staple forming pockets 66 formed thereon move toward the opposing staple cartridge 60.

Various clamping components can be used to effect opening and closing of the jaws 52, 54 to selectively clamp tissue therebetween. In the illustrated embodiment, the pivoting end 54*p* of the upper jaw 54 includes a closure feature 54*c* distal to its pivotal attachment with the staple channel 56. Thus, a closure tube 82, whose distal end includes a horseshoe aperture 82*a* that engages the closure feature 54*c*, selectively imparts an opening motion to the upper jaw 54 during proximal longitudinal motion and a closing motion to the upper jaw 54 during distal longitudinal motion of the closure tube 82 in response to the clamping trigger 22. It will be appreciated by a person skilled in the art that opening and closure of the end effector 50 may be effected by relative motion of the lower jaw 52 with respect to the upper jaw 54, relative motion of the upper jaw 54 with respect to the lower jaw 52, or by motion of both jaws 52, 54 with respect to one another.

Figure 5:
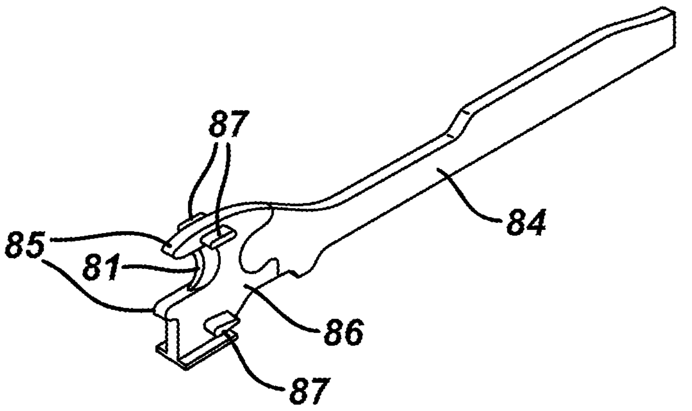
FIG. 5 is a perspective view of an E-beam component of the instrument of FIG. 3.

The firing components of the illustrated embodiment can include a firing bar 84, as shown in FIG. 5, having an E-beam 86 on a distal end thereof. The firing bar 84 is encompassed within the shaft 14, for example in a longitudinal firing bar slot 14*s* of the shaft 14, and guided by a firing motion from the handle 12. Actuation of the firing trigger 24 can affect distal motion of the E-beam 86 through at least a portion of the end effector 50 to thereby cause the firing of staples 70 contained within the staple cartridge 60. In the illustrated embodiment, guides 85 projecting from a distal end of the E-Beam 86 can engage a wedge sled 90, which in turn can push staple drivers 92 upwardly through staple cavities 68 formed in the staple cartridge 60. Upward movement of the staple drivers 92 applies an upward force on each of the plurality of staples 70 within the cartridge 60 to thereby push the staples 70 upwardly against the anvil surface 58 of the upper jaw 54 and to create formed staples 70'.

In addition to causing the firing of staples, the E-beam 86 can be configured to facilitate closure of the jaws 52, 54, spacing of the upper jaw 54 from the staple cartridge 60, and/or severing of tissue captured between the jaws 52, 54. In particular, a pair of top pins 87 and a pair of bottom pins 89 can engage one or both of the upper and lower jaws 52, 54 to compress the jaws 52, 54 toward one another as the firing bar 84 advances through the end effector 50. Simultaneously, a knife 81 extending between the top and bottom pins 87, 89 can be configured to sever tissue captured between the jaws 52, 54.

In use, the surgical stapler 10 can be disposed in a cannula or port and disposed at a surgical site. A tissue to be cut and stapled can be placed between the jaws 52, 54 of the surgical stapler 10. Features of the stapler 10 can be maneuvered as desired by the clinician to achieve a desired location of the jaws 52, 54 at the surgical site and the tissue with respect to the jaws 52, 54. After appropriate positioning has been achieved, the clamping trigger 22 can be pulled toward the stationary handle 20 to actuate the clamping system. The trigger 22 can cause components of the clamping system to operate such that the closure tube 82 advances distally through at least a portion of the shaft 14 to cause at least one of the jaws 52, 54 to collapse towards the other to clamp the tissue disposed therebetween. Thereafter, the trigger 24 can be pulled toward the stationary handle 20 to cause components of the firing system to operate such that the firing bar 84 and/or the E-beam 86 are advanced distally through at least a portion of the end effector 50 to effect the firing of staples 70 and optionally to sever the tissue captured between the jaws 52, 54.

Figure 6:
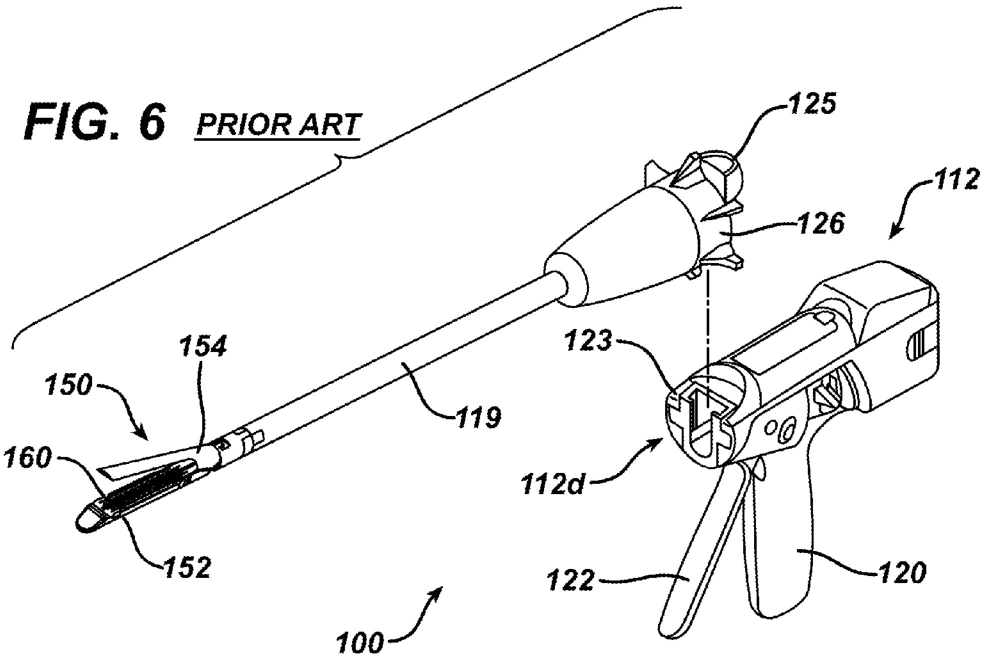
FIG. 6 is a perspective view of another prior art surgical instrument which can be used with one or more adjunct materials.

Another embodiment of a surgical instrument 100 is illustrated in FIG. 6. Like surgical instrument 10, surgical instrument 100 includes a handle assembly 112 with a shaft 114 extending distally therefrom and having an end effector 150 on a distal end thereof for treating tissue. Upper and lower jaws 154, 152 of the end effector 150 can be configured to capture tissue therebetween, staple the tissue by firing of staples from a cartridge 160 disposed in the lower jaw 154, and/or to create an incision in the tissue. In this embodiment, an attachment portion 116 on a proximal end of the shaft 114 can be configured to allow for removable attachment of the shaft 114 and the end effector 150 to the handle assembly 112. In particular, mating features 125 of the attachment portion 116 can mate to complementary mating features 123 of the handle assembly 112. The mating features 123, 125 can be configured to couple together via, e.g., a snap fit coupling, a bayonet type coupling, etc., although any number of complementary mating features and any type of coupling can be used to removably couple the shaft 114 to the handle assembly 112. Although the entire shaft 114 of the illustrated embodiment is configured to be detachable from the handle assembly 112, in some embodiments the attachment portion 116 can be configured to allow for detachment of only a distal portion of the shaft 114. Detachable coupling of the shaft 114 and/or the end effector 150 can allow for selective attachment of a desired end effector 150 for a particular procedure, and/or for reuse of the handle assembly 112 for multiple different procedures.

The handle assembly 112 can have one or more features thereon to manipulate and operate the end effector 150. By way of non-limiting example, a rotation knob 126 mounted on a distal end of the handle assembly 112 can facilitate rotation of the shaft 114 and/or the end effector 150 with respect to the handle assembly 112. The handle assembly 112 can further include clamping components as part of a clamping system actuated by trigger 122 and firing components as part of a firing system that can also be actuated by the trigger 122. Thus, in some embodiments, movement of the trigger 122 toward a stationary handle 120 through a first range of motion can actuate clamping components to cause opposed jaws 152, 154 to approximate toward one another to a closed position. Further movement of the trigger 122 toward the stationary handle 120 through a second range of motion can actuate firing components to cause the ejection of staples from the staple cartridge 160 and/or the advancement of a knife to sever tissue captured between the jaws 152, 154.

Figure 7:
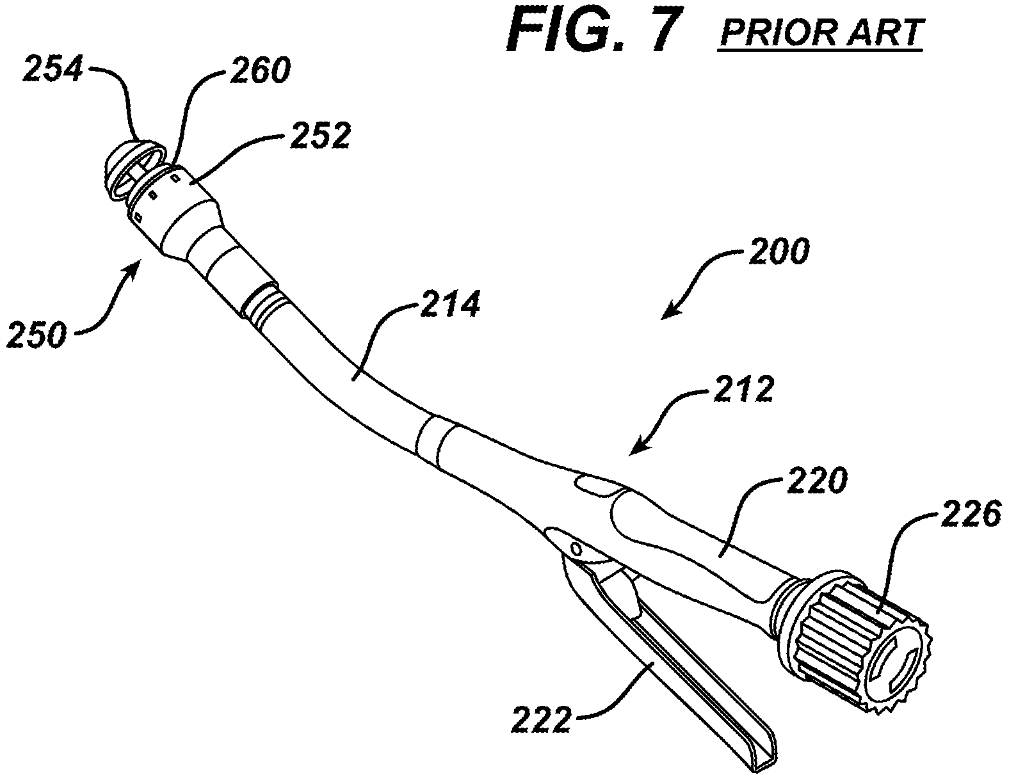
FIG. 7 is a perspective view of another prior art surgical instrument which can be used with one or more adjunct materials.

Yet another embodiment of a surgical instrument 200 is illustrated in FIG. 7. Like surgical instruments 10 and 100, surgical instrument 200 includes a handle assembly 212 with a shaft 214 extending distally therefrom and having an end effector 250 on a distal end thereof for treating tissue. The end effector 250 can include a cartridge assembly 252 and an anvil 254, each having a tissue-contacting surface 260*p*, 260*d* that is substantially circular in shape. The cartridge assembly 252 and anvil 254 can be coupled together via a shaft 262 extending from the anvil 254 to the handle assembly 212 of the stapler 200, and manipulating an actuator 222 on the handle assembly 220 can retract and advance the shaft 262 to move the anvil 254 relative to the cartridge assembly 252. In one embodiment, the shaft 262 can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The illustrated embodiments of surgical stapling instruments 10, 100, and 200 provide only a few examples of many different configurations, and associated methods of use, that can be used in conjunction with the disclosures provided herein. Although the illustrated embodiments are all configured for use in minimally invasive procedures, it will be appreciated that instruments configured for use in open surgical procedures, e.g., open linear staplers as described in U.S. Pat. No. 8,317,070, can be used in conjunction with the disclosures provided herein. Greater detail on the illustrated embodiments, as well as additional exemplary embodiments of surgical staplers, components thereof, and their related methods of use, that can be used in accordance with the present disclosure include those devices, components, and methods provided for in U.S. Publication No. 2013/0256377, U.S. Pat. No. 8,393,514, U.S. Pat. No. 8,317,070, U.S. Pat. No. 7,143,925, U.S. patent application Ser. No. 14/074,884, entitled "Sealing Materials for Use in Surgical Procedures, and filed on Nov. 8, 2013, U.S. patent application Ser. No. 14/074,810, entitled "Hybrid Adjunct Materials for Use in Surgical Stapling," and filed on Nov. 8, 2013, U.S. patent application Ser. No. 14/075,438, entitled "Positively Charged Implantable Materials and Method of Forming the Same," and filed on Nov. 8, 2013, U.S. patent application Ser. No. 14/075,459, entitled "Tissue Ingrowth Materials and Method of Using the Same," and filed on Nov. 8, 2013, U.S. patent application Ser. No. 14/074,902, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, each of which is incorporated by reference herein in its entirety.

End Effector Variations

End effectors of the surgical stapling instruments described herein can have one or more features for adjusting an amount of compression applied to tissue captured by the end effector. In some embodiments, the end effector can be configured to create a desired compression profile in tissue captured therein, for example a profile that helps to minimize bleeding, tearing, and/or leakage of the treated tissue. By way of non-limiting example, the desired tissue compression profile can be obtained using variations in a gap between upper and lower jaws of the end effector and/or variations in the orientation, size, and/or shape of staples applied to tissue by the end effector. As described in detail herein, adjunct material(s) used in conjunction with such an end effector can be configured to assist in creating the desired tissue compression profile and/or to accommodate features used to create the desired tissue compression profile.

Any such variations described herein can be used alone or together to provide the desired tissue compression profile. Although exemplary end effectors and components thereof are described in conjunction with a particular surgical instrument, e.g., instruments 10, 100, and 200, it will be appreciated that the end effectors and components thereof can be configured for use with other embodiments of surgical instruments as described herein.

Figure 8:
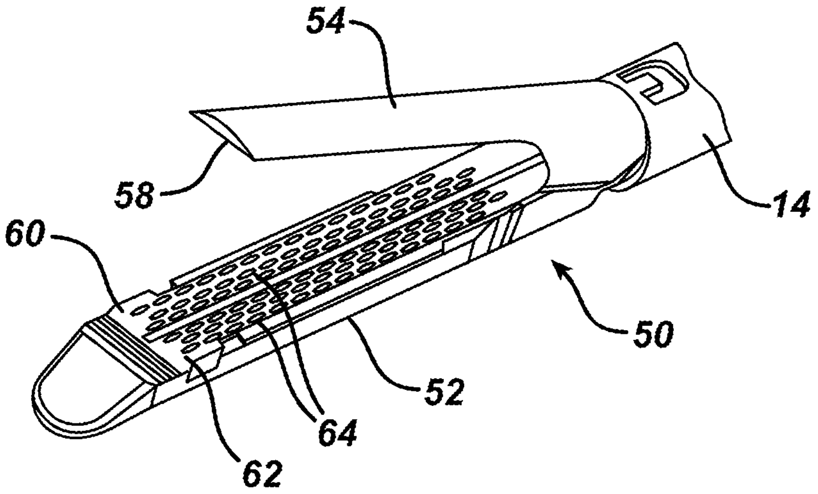
FIG. 8 is a perspective view of the end effector of FIG. 4.

In some embodiments, a staple cartridge disposed within an end effector of a surgical stapling instrument can have a first portion configured to compress tissue captured by the end effector more than a second portion when the end effector is in a closed position. The first portion of the cartridge can be spaced longitudinally and/or laterally from the second portion to create a desired compression gradient. For example, as shown in FIGS. 4 and 8, the staple cartridge 60 can have a stepped tissue contacting surface. In particular, the cartridge 60 can have an inner tissue contacting surface 62 and outer tissue contacting surfaces 64 that extend upwardly to a taller height than the inner tissue contacting surface 62. In this way, when the upper jaw 54 is in the closed position in close approximation with the cartridge 60, the anvil surface 58 can be configured to compress the outer surfaces 64 more than the inner surface 62 due to the taller height of the outer surfaces 64. In some circumstances, including circumstances where tissue positioned between the anvil surface 58 and the cartridge 60 has a constant, or at least substantially constant, thickness, the pressure generated within the tissue can be greater at outer portions of the end effector 50 than at inner portions of the end effector 50. Whereas a compression gradient generated by the cartridge 60 varies in a stepped manner, it will be appreciated by a person skilled in the art that a gradual compression gradient can be generated within the tissue by a gradual increase in height of various portions of the cartridge 60. It will also be appreciated that a compression gradient can be obtained by variations in height of the anvil surface 58, alone or in combination with height variations of the cartridge 60, and that height variations can be spaced laterally and/or longitudinally across the end effector 50.

Figure 9:
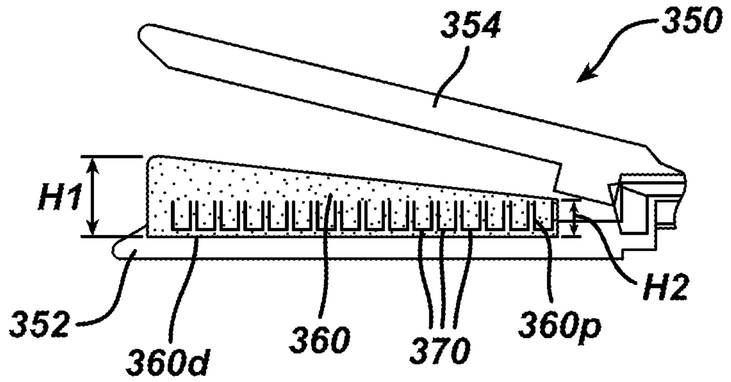
FIG. 9 is a side view of a prior art end effector having an implantable staple cartridge therein.

In some embodiments, one or more adjunct materials fixed to an end effector of a surgical stapling instrument can be used to create a desired compression profile in tissue captured by the end effector. Referring now to FIG. 9, a compressible, implantable staple cartridge 360 can be formed from one or more adjunct materials as described herein and can be configured to be seated within an end effector of a surgical instrument, e.g., an end effector 350. The cartridge 360 can have a height that decreases from a tallest height H1 at a distal end 360*d* thereof to a smallest height H2 at a proximal end 360*p* thereof. In this way, when an upper jaw 354 of the end effector 350 is in the closed position in close approximation with the cartridge 360, an upper jaw 354 of the end effector 350 can be configured to compress the distal end 360*d* more than the proximal end 360*p*. Although the compression gradient created in the captured tissue by the cartridge 360 decreases linearly from the distal end 360*d* to the proximal end 360*p*, it will appreciated by a person skilled in the art that any compression gradient can be created by different shapes of the cartridge 360. In at least one embodiment, a thickness of the cartridge 360 can vary across its width, similar to the cartridge 360.

Figure 10:
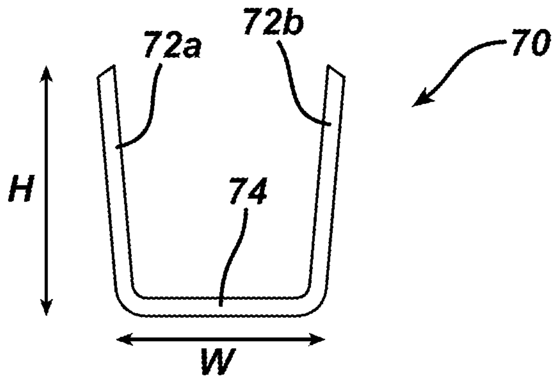
FIG. 10 is a side view of a prior art staple.
Figure 11:
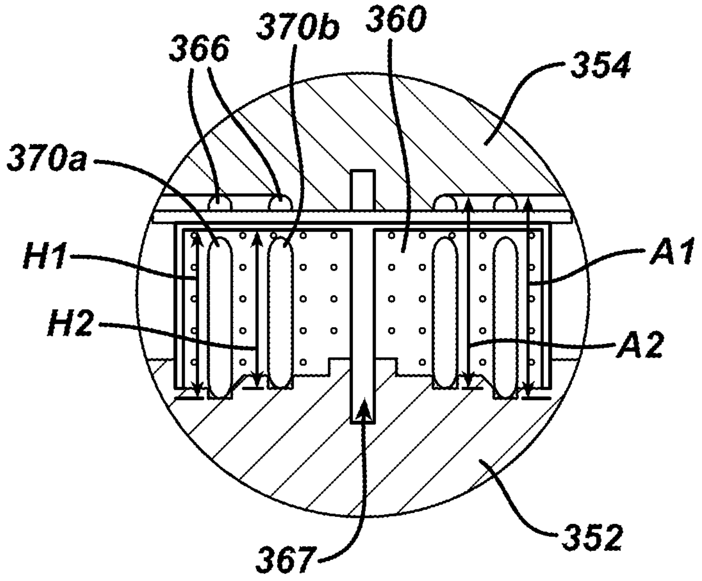
FIG. 11 is a cross-sectional view of the end effector of FIG. 9.

In some embodiments, staples contained within a staple cartridge of an end effector can be configured to create a desired compression profile within tissue captured by the staples. The desired compression profile can be created in stapled tissue, for example, where staples within the staple cartridge have different unformed staple heights. As shown in FIG. 10, an unformed height H of the exemplary staple 70 can be measured from a base 74 of the staple 70 to a top, or tip, of legs 72*a*, 72*b* of the staple 70. Referring now to FIG. 11, which illustrates a cross section of the end effector 350, a first group of staples 370*a* can have first staple height H1 that is taller than a second staple height H2 of a second group of staples 370*b*. The first group of the staples 370*a* can be positioned in a first portion of the staple cartridge 360, for example in an outer portion, and the second group of staples 370*b* can be positioned in a second portion of the staple cartridge 360, for example in an inner portion. In the illustrated embodiment, the cartridge 360, and therefore the compression gradient, can be configured to be symmetrical about a slot 367 configured to receive a cutting instrument, e.g., the E-beam 86, therethrough. It will be appreciated by a person skilled in the art that the first and second groups of staples 370*a*, 370*b* can be arranged in any pattern and can be spaced laterally and/or longitudinally along the cartridge 360. In certain embodiments, a plurality of staple groups, each group having different unformed staple heights, can be utilized. In at least one such embodiment, a third group having an intermediate staple height can be positioned in the cartridge intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

Figure 12:
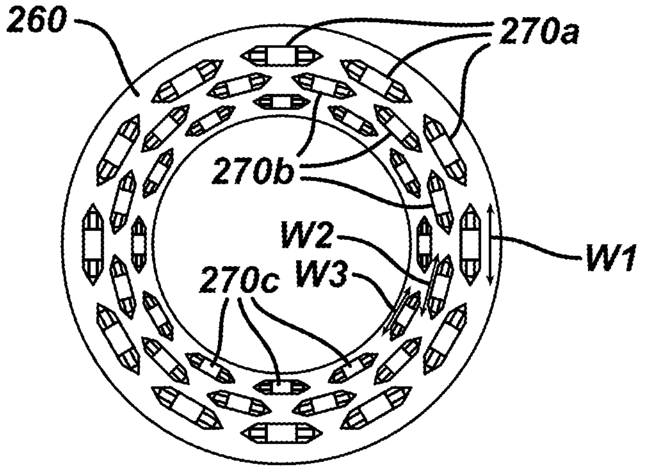
FIG. 12 is a top view of a prior art staple cartridge for use with the instrument of FIG. 7.

Similarly, staples within a staple cartridge can have different crown widths to create a desired compression profile in the stapled tissue. As shown in FIG. 10, a crown width W of the exemplary staple 70 can be measured from one side of the base 74 of the staple 70 to an opposite side. Like the above-described variations in staple height H, variations in the staple width W can be spaced throughout the staple cartridge to create a plurality of staple groups dispersed longitudinally and/or laterally across the cartridge. By way of non-limiting example, FIG. 12 illustrates a staple cartridge 260 for use with the surgical instrument 200 and having staples 270 therein with different crown widths W. The staple cartridge 260 houses three groups of staples 270*a*, 270*b*, 270*c*, each having different widths W1, W2, and W3, respectively, although any number of staple groups is possible. As shown, the groups of staples 270*a*, 270*b*, 270*c* can be arranged in circumferential rows, with the staples 270*c* having the largest width W1 positioned on an outermost edge of the cartridge 260 and the staples 270*a* having the smallest width W3 positioned on an innermost edge of the cartridge 260. In other embodiments, staples having a larger crown width can be positioned near an inner most edge of a cartridge and staples having a smaller crown width can be positioned near an outer edge of the cartridge. In still further embodiments, staples along the same row can have different crown widths.

Figure 13:
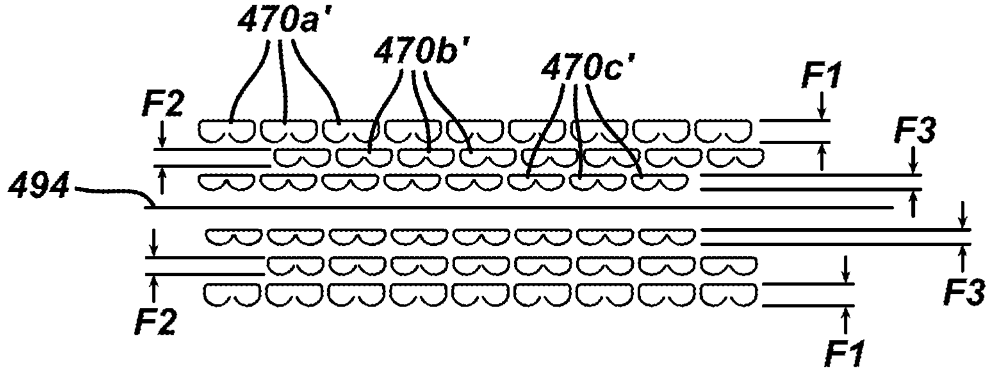
FIG. 13 is a diagrammatic representation of lines of staples installed using a prior art surgical stapling instrument.

Additionally or alternatively, it may be possible to create a desired tissue compression profile by the creation of different formed (final) staple heights. FIG. 13 illustrates an exemplary embodiment of lines of formed staples 470' installed using a surgical stapling instrument as described herein and configured to apply staples 470' having different formed heights as well as to cut tissue to thereby create a cut line 494. As shown in FIG. 13, formed heights F1 of a first group of staples 470*a'* in a first row that is the farthest distance away from the cut line 494 are greater than formed heights F3 of a third group of staples 470*c'* in a third row that is closest to the cut line 494. A second group of staples 470*b'* in a second row that is formed between the first and third rows can have staples 470*b'* with a formed height F2 that is between the heights F1, F3. In other embodiments, formed heights of the staples can decrease from an innermost row to an outermost row. In still further embodiments, formed heights of the staples in a single row can increase or decrease from staple to staple.

Referring again to FIG. 11, differences in formed staple heights can be attained by, for example, altering a staple forming distance A. Forming distances A1, A2 can be measured from a seat of staples 370*a*, 370*b*, respectively, within the cartridge 360, and an apex of a corresponding forming pocket 366 of the anvil surface 358 when the upper jaw 354 is in the closed position. In one embodiment, for example, a first staple forming distance A1 is different from a second staple forming distance A2. Because the forming distance A1 is greater than the forming distance A2, the staples 370*a* are not compressed as much as the staples 370*b*, which can alter the formed heights of the staples 370*a*, 370*b*. In particular, greater amounts of compression, corresponding to smaller forming distances, can result in staples with smaller formed (final) heights. It will be understood that similar results may be attained in any desired pattern.

Figure 14:
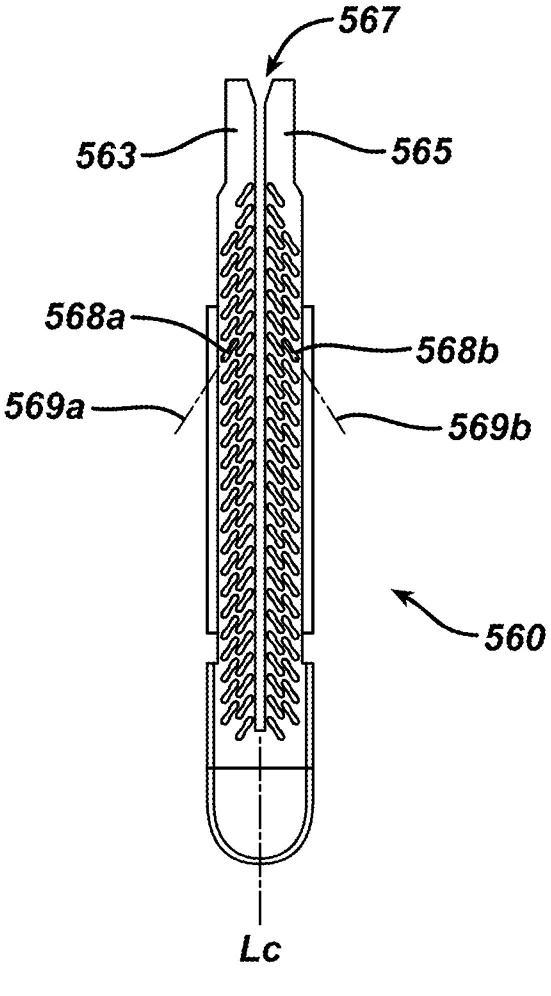
FIG. 14 is a top view of a prior art staple cartridge having a staple pattern.
Figure 15:
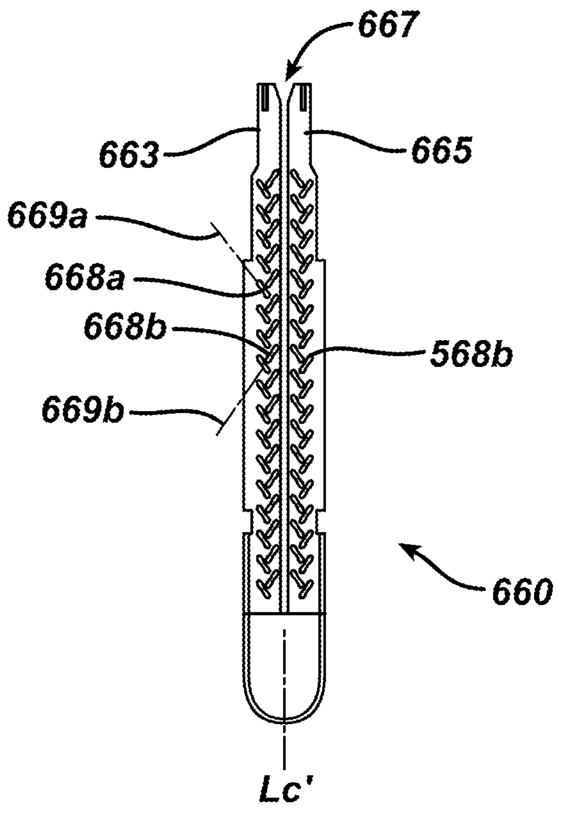
FIG. 15 is a side view of an end effector with a staple cartridge loaded with an adjunct material.

Varied tissue compression gradients can be obtained via patterns in staple orientation within a staple cartridge, for example by the patterns illustrated in FIGS. 14 and 15. In the embodiment depicted in FIG. 14, staple cartridge 560 can include at least one first staple cavity 568*a* and at least one second staple cavity 568*b* for housing staples 570 therein. The first cavity 568*a* can be situated on first lateral side 563 of the cartridge 560 and the second cavity 568*b* can be situated on a second lateral side 565 of the cartridge 560, the first and second lateral sides 563, 565 being separated by a slot 567 configured to receive a cutting instrument, e.g., the E-beam 86, therethrough. The first cavity 568*a* can define a first longitudinal axis 569*a* and the second cavity 568*b* can define a second longitudinal axis 569*b*. In the illustrated embodiment, the first axis 569*a* is perpendicular, or substantially perpendicular, to the second axis 569*b*. In other embodiments, the first axis 569*a* can be transverse to the second axis 569*b* such that axes 569*a*, 569*b* can create an acute or obtuse angle therebetween. In still other embodiments, the first axis 569*a* can be parallel to, or substantially parallel to, the second axis 569*b*. In some embodiments, at least a portion of the staple cavities 568*a*, 568*b* can overlap, such that staples 570 therein can be interlocked when formed. The cartridge 560 can have a plurality of each of the first and second cavities 568*a*, 568*b*, which can be arranged in any pattern on first and second sides 563, 565 of the cartridge 560, for example in rows extending along both sides 563, 565 of the cartridge 560 along a longitudinal axis Lc of the cartridge 560. The staples 570 housed within the cavities 568*a*, 568*b* can be implanted into tissue in a pattern determined by the orientation and positioning of the cavities 568*a*, 568*b*. The cartridge 560, for example, can be used to implant staples 570 having different orientations of the staples 570 on opposite sides of an incision line created by a surgical instrument carrying the cartridge 560.

In other embodiments, for example the embodiment of a cartridge 660 illustrated in FIG. 15, staple cavities 668*a* and 668*b* having different orientations can both be disposed on a single lateral side of the cartridge 660. As shown in FIG. 15, an axis 669*a* of the first staple cavity 668*a* is perpendicular, or substantially perpendicular, to an axis 669*b* of the second staple cavity 668*b*, both of which are disposed on each of first and second lateral sides 663, 665 of the cartridge 660. In other embodiments, the axes 669*a*, 669*b* can form an acute or obtuse angle therebetween, or can be parallel to one another. A plurality of the first and second cavities 668*a*, 668*b* can be aligned in adjacent rows along a longitudinal axis Lc' of the cartridge 660 on each of the first and second sides 663, 665 of the cartridge 660. In this embodiment, staples 670 housed within the cavities 668*a*, 668*b* can be implanted into tissue in a symmetrical pattern about an incision line created by a surgical instrument carrying the cartridge 660. Greater detail on staple patterns, as well as additional embodiments of such patterns, can be found in U.S. Publication No. 2011/0192882, incorporated herein by reference in its entirety.

Exemplary Compositions for Adjunct Materials

Figure 16:
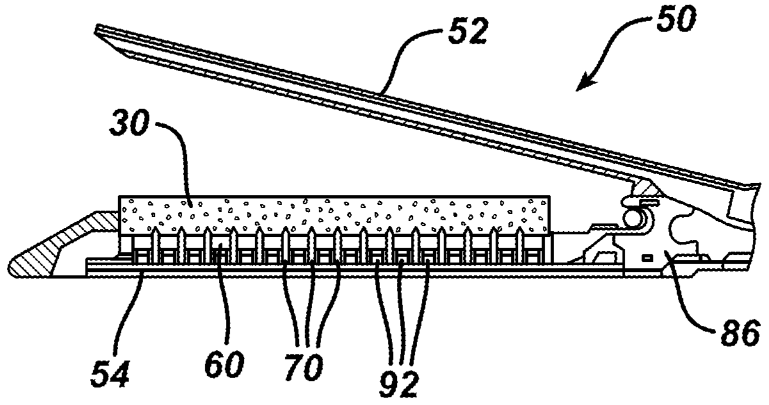
FIG. 16 is a side, cross-sectional view of the end effector of FIG. 4 having an adjunct material thereon.

Regardless of the configuration of the surgical instrument, the present disclosure provides for the use of implantable materials, e.g., synthetic and/or biological materials, collectively “adjunct materials,” in conjunction with instrument operations. As shown in FIG. 16, the end effector 50 can include at least one piece of adjunct material 30 positioned intermediate the lower and upper jaw members 52, 54 and it can be releasably retained to one of the staple channel 56 and/or the anvil surface 58. In use, the adjunct material 30 and patient tissue can be captured by staples 70 when the staples 70 are fired. Then, the adjunct material 30 can be separated from the surgical stapler and can remain in the patient when the stapler is removed from the patient. Exemplary devices and methods for attaching one or more adjunct materials to an end effector of a surgical instrument can be found in U.S. Publication No. 2013/0256377 and U.S. Publication No. 2013/0153641, incorporated herein by reference in their entirety.

Adjunct material used in conjunction with the disclosures provided for herein can have any number of configurations and properties. Generally, they can be made from a bioabsorbable material, a biofragmentable material, and/or a material otherwise capable of being broken down, for example, such that the adjunct material can be absorbed, dissolved, fragmented, and/or broken down during the healing process. In at least one embodiment, the adjunct material can be configured to degrade over time to form a gel, e.g., a sealant, to assist in wound healing. In other embodiments, the adjunct material can include a therapeutic drug that can be configured to be released over time to aid the tissue in healing, for example. In further various embodiments, the adjunct materials can include a non-absorbable and/or a material not capable of being broken down, for example.

Some particularly advantageous adjunct materials can include porous polymer scaffolds that can be configured to be broken down, for example by exposure to water such that the water attacks the linkage of a polymer of the material. The degraded material can be configured to gel over a wound site to thereby coat the wounded tissue, e.g., wounded soft tissue, which can aid in compressing, sealing and/or generally creating an environment at the wound site that promotes healing of the tissue. In particular, such degradable polymers can allow for the tissue itself to become the weight-bearing component. In some embodiments, the degraded material can include chemoattractant agents that attract natural healing compounds to the wound site. The polymer scaffolds can be configured to have a desired rate of degradation, for example within minutes to hours after attachment to tissue, to thereby assist in the healing process almost immediately after attachment. For more details on porous polymer scaffolds as described herein, see Q. Chen et al., Elastomeric biomaterials for tissue engineering, Progress in Polymer Science 38 (2013) 584-671, incorporated herein by reference in its entirety.

In some embodiments, the porous polymer scaffolds described herein can be physically crosslinked, which can allow for shaping of the polymer into various complicated three-dimensional shapes, e.g., fibers, sheets, films etc., having any desired porosity, surface-to-volume ratio, and mechanical properties. The scaffold can be shaped into a desired form via a number of methods, for example by extrusion, wet spinning, electrospinning, thermally induced phase separation (TIPS), salt leaching/freeze-drying, etc. Where the scaffold is formed into a film or sheet, the film or sheet can have any desired thickness, for example in a range of about 50 to 750 μm or in a range of about 1 to 3 mm, depending on the desired application.

One embodiment of a porous polymer scaffold includes multiple layers, each of which can perform different wound healing functions. In an exemplary embodiment, the scaffold includes three layers. The first layer can be made from polyester carbonate urethane urea (PECUU), the second layer can be made from poly(ester urethane) urea (PEUU), and the third layer can be made from poly(carbonate urethane) urea (PCUU) lysine triisocyanate (LTI) or hexamethylene diisocyanate (HDI). A person skilled in the art will appreciate that the properties of each layer can be optimized to achieve desired results and performance. In some embodiments, the desired properties of the scaffold can be achieved by blending or copolymerizing the material of the third layer or copolymerized with various polymers or copolymers. By way of non-limiting examples, the material of the third layer can be blended with a polyester copolymer, for example polycaprolactone (PCL), polyglycolic acid PGA, poly(D,L-lactic acid) (PDLLA), PGA, and/or polyethylene glycol (PEG). Where the material of the third layer is blended with both the polyester copolymer and the PEG, a ratio of the polyester to the PEG in the third layer can be about 50:50. In another exemplary embodiment, the PCL can be present in a range of about 60-70% weight/volume, the PGA can be present in a range of about 20-30% weight/volume, the PEG can be present in a range of about 50% weight/volume, and the PDLLA can be present in a range of about 10% weight/volume.

The three-layered film can be configured to degrade almost immediately upon attachment to tissue, for example within about 1 to 2 hours after attachment, although each of the three layers can be configured to degrade differently to have different healing benefits. The order, number, and thickness of each of the layers can vary, and can be tailored to create desired degradation and/or compression ratios. In some embodiments, the first, second, and third layers can be formed on top of a base material or substrate, for example on top of PCL, which can be configured to aid in mechanical compression of the wounded tissue.

Another exemplary embodiment of a porous polymer scaffold can be synthesized from polyhydroxyalkanoate (PHA). In an exemplary embodiment, the PHA can be naturally produced from a variety of microorganisms, e.g., Gram-negative or Gram-positive bacteria, or it can be synthesized, e.g., similar to the production of Biopol®, available from Zeneca of London, United Kingdom. Because PHAs are very quick to dissolve, scaffolds made from PHA can begin to degrade within 20 to 30 minutes after attachment to tissue via contact with heat and/or water. Where the PHA scaffold has a higher molecular weight, the degradation time can be higher, for example in a range of about 30 minutes to about 10 hours. The PHA can be formed into a very thin film, for example a film having a thickness of less than 0.1 mm, e.g., in a range of between 50 to 750 μm. In some embodiments, the PHA can be copolymerized and/or blended with one or more additional materials. By way of non-limiting example, the PHA can be copolymerized with hydroxlvalerate (HV), hydroxylbutyrate (HB), and/or hydroxylhexanoate (HH), which can reduce a level or crystallinity and/or brittleness of the PHA. In other embodiments, the PHA can be blended with one or more thermoplastics, e.g., poly(lactic acid) (PLA), PGA, PCL, starch, etc., to thereby customize a molecular weight and resultant mechanical properties of the scaffold. In certain aspects, one or more of the polymers can be a thermoplastic polymer.

In other embodiments, the scaffold can be synthesized from poly(polyol sebacate) (PPS), e.g., from poly(glycerol-sebacate) (PGS). Such scaffolds can be particularly biocompatible and can provide an additional advantage of reducing a risk of infection in addition to promoting healing. Other exemplary embodiments can be synthesized from xylitol-based elastomers, for example polyxylitol sebacates (PXSs), which can offer structural stability over a clinically required period and/or can enter the metabolic pathway slowly without causing rapid fluctuations of blood glucose levels. Scaffolds made from PXS's can be formed into a thicker film to thereby provide greater compression to the wound site, and can be configured to degrade within a range of about 10 hours to 8 days after attachment. Still other exemplary embodiments can be synthesized from poly(glycerol sebacate-co-acrylate) (PGSA), which can promote tissue ingrowth into the scaffold, particularly when formed as a fiber, and/or can serve as an antibacterial agent. PGSA scaffolds can be useful as a replacement for traditional surgical sutures and staples, and/or can serve as a waterproof sealant for hollow organ anastomoses (e.g., ducts, intestine, etc.), 2D mesh grafts (e.g., treatment of hernias, ulcers, burns, etc.), and/or wound dressings (e.g., hemostatic patches, etc.). The PGSA can be combined with glycerol, which can allow the scaffold to last longer in situ, for example up to 20 days.

In yet another embodiment, the scaffold can be made from poly(ϵ-caprolactone) (PCL), which can be blended with silk fibroin (SF) and which can be formed into a very thin film. The PCL/SF blend can have highly biocompatible properties and/or can improve cell attachment and/or proliferation to the scaffold. For example, when implanted onto tissue, the scaffold can release fibroin into the tissue to thereby promote faster healing, nearly immediate hemostasis, and/or to attract fibroblasts in greater numbers. The PCL component can further assist in the healing process by providing mechanical compression of the wounded tissue. A higher PCL content can provide better mechanical properties, while a higher SF content can provide better degradation properties. In general, the PCL content can be in a range of about 50 to 90% weight/volume and the SF content can be in a range of about 10 to 50% weight/volume. More details on the properties and manufacturing methods for scaffolds made from PCL and SF can be found in Jun Sik Lim et al., Fabrication and Evaluation of Poly(epsilon-caprolactone)/Silk Fibroin Blend Nanofibrous Scaffold, Biopolymers 97: 265-275 (2012), incorporated herein by reference in its entirety.

In still further embodiments, the scaffold can include PCL coated with a gelatin. The scaffold can be arranged in one or more layers, for example with the PCL serving as a substrate. The PCL can function to increase a mechanical strength of the scaffold and/or can support fibroblast adhesion and cell proliferation. More details on the properties and manufacturing methods for scaffolds made from gelatin-coated PCL can be found in Pengcheng Zhao et al., Biodegradable fibrous scaffolds composed of gelatin coated poly (ϵ-caprolactone) prepared by coaxial electrospinning, J. Biomed Mater Res 83A: 372-382 (2007), incorporated herein by reference in its entirety.

Table 1 below outlines exemplary molecular weight ranges, approximate absorption times, and average dimensions of films made from the aforementioned porous polymer scaffold materials. It will be appreciated by a person skilled in the art that the ranges provided in Table 1 are not intended to be limiting, and that a molecular weight of any of the polymers described herein can be altered to obtain the desired degradation properties.

TABLE 1

| Film | Average molecular weight in Daltons | Approximate absorption times | Average thickness | Average length | Average width |
|---|---|---|---|---|---|
| Polyester carbonate urethane urea (PECUU) | 5,000 to 80,000 | 14 to 60 days | 10 μm to 1 mil | 25.4 to 100 mm | 10.3 to 12.7 mm |
| Poly(ester urethane)urea (PEUU) | 5,000 to 80,000 | 14 to 60 days | 10 μm to 1 mil | 25.4 to 100 mm | 10.3 to 12.7 mm |
| Poly(carbonate | 10,000 to 200,000 | 14 to 60 days | 100 μm to 1 mil | 25.4 to 100 mm | 10.3 to 12.7 mm |

TABLE 1-continued

| Film | Average molecular weight in Daltons | Approximate absorption times | Average thickness | Average length | Average width |
|---|---|---|---|---|---|
| urethane)urea (PCUU) | (preferably 15,000 to 50,000) | | | | |
| Polyhydroxyalkanoate (PHA) | 2.107 × 1029 to 2.589 × 1029 | 7 to 60 days | 100 μm to 1 mil | 25.4 to 100 mm | 10.3 to 12.7 mm |
| Poly(polyol sebacate) (PPS) | 89,000 and 124,000 | 7 to 60 days | 100 μm to 1 mil | 25.4 to 100 mm | 10.3 to 12.7 mm |
| Polyxylitol sebacates (PXS's) | 1.47 × 1027 to 3.73 × 1027 | 7 to 60 days | 100 μm to 1 mil | 25.4 to 100 mm | 10.3 to 12.7 mm |
| Poly(glycerol sebacate-co-acrylate) (PGSA) | 5.8 × 1026 to 7.5 × 1026 | 7 to 60 days | 10 μm to 1 mil | 25.4 to 100 mm | 10.3 to 12.7 mm |
| Poly(ϵ-caprolactone); silk fibroin; scaffold (PCL/SF) Blend PCL/SF (50/50) | 25,000 to 325,000 (SF) 4.21 × 1028 to 4.81 × 1028 (PCL) | 21 to 60 days (SF) 2 to 3 years (PCL) | 10 μm to 1 mil | 25.4 to 100 mm | 10.3 to 12.7 mm |
| Gelatin coated PCL (poly (ϵ-caprolactone) | 3.01 × 1028 to 1.98 × 1029 (gelatin) 4.21 × 1028 to 4.81 × 1028 (PCL) | 7 days (gelatin) 2 to 3 years (PCL) | 100 μm to 1 mil | 25.4 to 100 mm | 10.3 to 12.7 mm |

Other suitable adjunct materials can include absorbable polyurethanes, e.g., polyurethanes derived from aromatic absorbable isocyanates that can be similar to methylene bis(phenyl isocyanate) (MDI) and chain extender diols. The absorbable polyurethanes can be configured to hydrolytically degrade into safe and biocompatible products upon hydrolysis. Non-limiting examples of hydrolysable aromatic isocyanates that can be used to form the absorbable polyurethanes include glycolate-diisocyante, caprolactone-diisocyanate, glycolate-ethylene glycol-glycolate, glycolate-diethylene glycol-glycolate, lactate-diethylene glycol-lactate, trimester of gycolic acid with trimethylpropane, and tetraester of glycolic acid with pentaerythritol.

Another particularly advantageous adjunct material that can be used in conjunction with the disclosures provided herein are the materials that form the multilayered dressings disclosed in U.S. Publication No. 2006/0257458, incorporated herein in its entirety, which are particularly suited to absorb and retain fluids when compressed, e.g., by the application of staples. Other exemplary, non-limiting examples of synthetic materials that can be used in conjunction with the disclosures provided for herein, e.g., as a buttress, include biodegradable synthetic absorbable polymer such as a polydioxanon film sold under the trademark PDS® or with a Polyglycerol sebacate (PGS) film or other biodegradable films formed from PGA (Polyglycolic acid and various forms thereof, marketed under the trademarks Vicryl, Dexon, and/or Neoveil), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin 910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), polydioxanone (PDO) and various forms thereof (e.g., marketed under the trademark PDS) or a blend or copolymerization of any of the above. Blends and/or copolymerizations of any of the aforementioned materials can be tailored to have a desired molecular weight and/or degradation rate.

Some non-limiting examples of biologic derived materials that can be used in conjunction with the disclosures provided for herein, e.g., as a sealant material, include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized regenerated cellulose, regenerated cellulose, mussel-based adhesive, poly (amino acid), agarose, polyetheretherketones, amylose, hyaluronan, hyaluronic acid, whey protein, cellulose gum, starch, gelatin, silk, Progel®, available from Davol Inc. of Warwick, R.I., TachoSil®, available from Baxter of Deerfield, Ill., or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Pat. No. 7,772,352, PCT Publication No. WO 2014/016819, U.S. Patent Application Publication No. 2006/0257458, U.S. Patent Application Publication No. 2012/0080335, U.S. Patent Application Publication No. 2012/0083835, U.S. Patent Application Publication No. 2013/0256372, U.S. Patent Application Publication No. 2013/0256365, U.S. Patent Application Publication No. 2013/0256376, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

Adjuncts Having Tissue Reinforcement Features

Adjunct materials described herein may be used in any suitable type of surgery where a surgical stapler or other instrument is deployed to connect tissues. One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

In some embodiments, adjunct materials described herein may be used for sealing staple punctures created when a surgical stapler is used in lung surgery. When surgery is performed on a lung, the lung is typically collapsed, and a required procedure, including application of the stapler to lung tissue, is then performed on the collapsed lung. After the procedure is completed, the collapsed lung is reinflated to a normal lung volume. The reinflation of the lung stretches the lung tissue (e.g., lung parenchyma), particularly in an area around a staple line, which may result in increased stress at a junction between the stapled tissue (which is restricted from stretching by the staples) and the surrounding tissue areas. Furthermore, an airtight sealing is required for the staple punctures of the lung. The sealing of a good quality may be difficult to achieve—while leaks around staple punctures typically seal within approximately five days, in some cases, staple punctures may persist for longer periods of time, such as, for example, six months or longer. In such circumstances, a lengthy hospitalization of a patient may be required.

Accordingly, applicants have recognized and appreciated that an end effector, such as a staple cartridge assembly for use with a surgical stapler, and/or its associated anvil, can include an adjunct material which may be used to seal punctures created by a surgical stapler used to secure lung or other types of tissue. The adjunct material can also reinforce the staple line, distribute stress load on the tissue near the staple line, and minimize tearing of the tissue—e.g., when the lung tissue is reinflated after the surgery to transition to its normal volume.

In some embodiments, the staple cartridge assembly can comprise a cartridge body of a surgical stapler and an adjunct material, which is interchangeably referred to herein as a tissue reinforcement construct. The tissue reinforcement construct can be removably attached to the cartridge body and is configured to be delivered to a surgical site by deployment of the staples of the surgical stapler. When the staples are deployed, the adjunct material can remain at the surgical site with the staples. In this way, the adjunct material can be used to help seal holes formed by staples and/or can be used to provide tissue reinforcement at the treatment site.

In some embodiments, the adjunct material can comprise a first, or outer, dissolvable and/or absorbable material encompassing a second, or inner, material. The first material can be selectively dissolvable and/or absorbable. In some embodiments, the first material may be brittle. The second material can be a swellable, hydrophilic material that is maintained within the first material in a constrained configuration and is configured to transition to a predetermined shape when exposed to moisture in an unconstrained configuration. Prior to deployment of the staples, the second material can be encompassed within the first material in an intact form.

In some embodiments, the first material can be less hydrophilic than the second material and can therefore serve as a moisture barrier. The second material may be compressed within the first material in a constrained configuration such that, when the first material is punctured by staples deployed to connect tissue or is otherwise penetrated (e.g., cut by a surgical knife or compressed between a cartridge and anvil), the second material is exposed to moisture from the surrounding environment of the patient's body and begins to swell. In this way, the second material gradually swells and expands to eventually transition to a predetermined shape. As the second inner material swells, it expands to seal the holes in the tissue created by the staples. The second material can swell at a rate that allows it to form a seal around a hole as the tissue, such as lung parenchyma that was deflated prior to a surgical procedure, is inflated back to its normal volume, while compressing the stretching tissue and restricting its deformation or preventing its tearing around the staple line.

In some embodiments, one or more portions of the first material, such as, for example, portions encompassing peripheral edges of the second material can be more dissolvable than portions of the first material encompassing a central portion of the second material. Additionally the portions of the first material encompassing the peripheral edges of the second material can be more absorbable than portions of the first material encompassing the central portion of the second material. After the integrity of the first material is broken and as the portions of the first material encompassing the peripheral edges of the second material are dissolved or absorbed by the patient's body, the second material enclosed within those portion is allowed to expand upon exposure to moisture to thus seal and reinforce the stapled tissue.

The first and second materials of the adjunct material may comprise any suitable materials. In some embodiments, it is advantageous to select a material that is absorbable and capable of bearing compressive and bending loads. The first material can be formed from a variety of materials. They may be present in continuous form so as to fully encapsulate the materials making up the center of the device, or alternately they might be present in a non-continuous form. These non-continuous forms include, but are not limited to, otherwise encapsulating forms with minute openings allowing water or bodily fluids to access the materials making up the center of the device to facilitate rapid hydration to allow expansion of the center material; melt blend nonwoven forms with controlled porosity; immiscible polymer blends having a major blend component an absorbable polymer and a minor component being a biocompatible water soluble polymer which is capable of rapidly dissolving creating conduits to the central material allowing for its rapid hydration to generate an external force on the tissue.

The absorbable polymer making up the outer layer, although not limited to, can be selected from among polydioxanone (also referred to as poly(1,4-dioxan-2-one), or poly(p-dioxanone)); polyglycolide (also referred to as polyglycolic acid), polylactide (also referred to as polylactic acid) in all its forms based on the ring-opening of the corresponding lactone monomers, L(−)-lactide, D(+)-lactide, and meso-lactide, as well as all of its forms based upon polycondensation of L(+)-lactic acid and D(−)-lactic acid (e.g., poly(L(−)-lactide), poly(D(+)-lactide), poly(meso-lactide), poly(racemic-lactide), poly(L-lactic acid), poly(D-lactic acid), etc.); the polycaprolactones, especially poly(epsilon-caprolactone); polyhydroxyalkanoate (PHA); the absorbable copolymers usually formed by the ring-opening polymerization of the lactone monomers, L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. These later copolymers include, but are not limited to epsilon-caprolactone/glycolide copolymers such as 25/75 poly(caprolactone-co-glycolide) (also referred to as poliglecaprone 25), 10/90 poly(L(−)-lacide-co-glycolide) (also referred to as polyglactin 910), polyglyconate, polyglycolide-trimethylene carbonate (PGA/TMC). The absorbable polymer can be a miscible or immiscible blend of the previously mentioned polymers (and copolymers thereof) in any combination. In other embodiments, the first material may be selected from biodegradable synthetic absorbable polymers such as a polydioxanon film sold under the trademark PDS® or with a Polyglycerol sebacate (PGS) film or other biodegradable films formed from PGA (Polyglycolic acid and various forms thereof, marketed under the trademarks Vicryl® and/or Neoveil®), PCL (Polycaprolactone), PLA or PLLA (Polylactic acid), PHA (polyhydroxyalkanoate), PGCL (poliglecaprone 25, sold under the trademark Monocryl®), PANACRYL® (Ethicon, Inc., Somerville, N.J.), polyglactin 910, poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), absorbable polyurethanes, or a blend or copolymerization of any of the above. Blends and/or copolymerizations of any of the aforementioned materials can be tailored to have a desired molecular weight and/or degradation rate. It will be clear to one skilled in the art to select a biocompatible material.

The second material may be formed from a variety of materials. Advantageous materials include those that are absorbable and can undergo a controlled degree of swelling so as to create an external force on the tissue. Swelling might be accomplished by hydration based on an influx of water or bodily fluids. One class of materials that is particularly advantageous is absorbable dehydrated hydrogels. These include the materials described in U.S. Pat. No. 5,698,213, entitled "Hydrogels of Absorbable Polyoxaesters" and crosslinked aliphatic polyoxaesters containing amine and/or amido groups and blends thereof with other polymers as described in U.S. Pat. No. 5,700,583, each of which is incorporated herein by reference in its entirety. Other materials suitable for the second material include water soluble polymers such as poly(vinylpyrrolidone) (PVP), poly(vinyl alcohol) (PVA), and polyethylene glycol (PEG) or the higher molecular weight polyethylene oxide (PEO). Additionally suitable are absorbable polyurethanes. It is to be understood that suitable materials include copolymers that contain a hydrophilic section and an absorbable polyester section; this would include, by way of example, the copolymer made by reaction of a relatively low molecular weight alpha,omega-dihydroxy polyethylene glycol and a lactone monomer such as L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. Blends of materials and copolymers formed from a wide variety of suitable monomers, some already mentioned above, may be suitable. In one embodiment, the second material may also be a biologically derived material as described above such as ORC. It will be clear to one skilled in the art to select a biocompatible material.

The adjunct material described herein can be delivered to a treatment site using any suitable surgical stapling device, as embodiments are not limited to any specific methods of employing a surgical stapling device that in used in conjunction with the adjunct material. In some embodiments, tissue is engaged between a cartridge assembly and an anvil of a surgical stapler at a treatment site, wherein at least one of the cartridge assembly and anvil has an adjunct material removably retained thereon. The surgical stapler can then be actuated to eject staples from the cartridge assembly through the adjunct material and into the tissue. The adjunct material can help to reduce impact and trauma from the stapling and distribute stress load on the tissue near the staple line to reduce the possibility of tissue tearing.

Figure 17A:
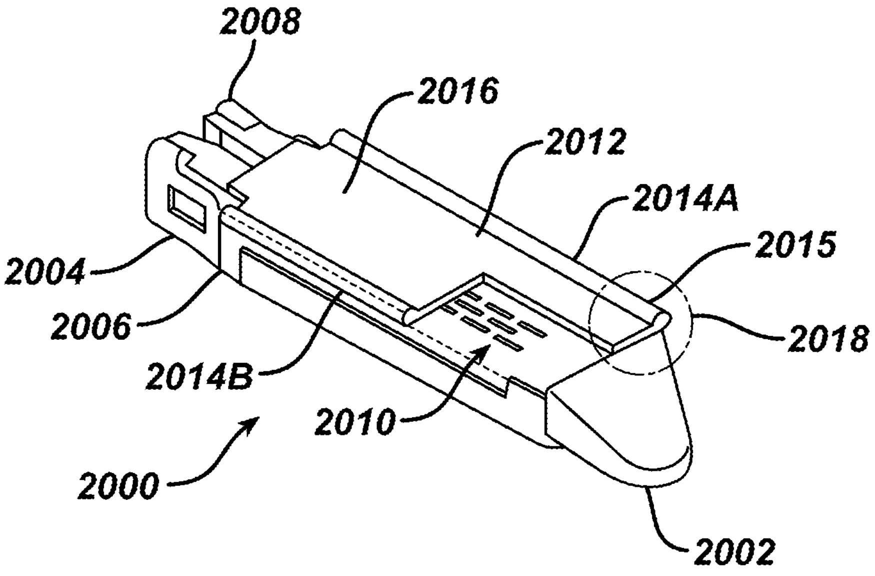
FIG. 17A is a perspective view of a staple cartridge assembly comprising an adjunct material, in accordance with some embodiments.

FIG. 17A illustrates an example of a portion 2000 of an end effector of a surgical stapler that can be used with one or more adjunct materials as described herein. In the example illustrated, the portion is a jaw 2000 having a distal end 2002, a proximal end 2004 and a cartridge body 2006. As shown in FIG. 17A, the surgical stapler includes a shaft 2008 that can be configured to couple the end effector with a handle assembly of the surgical stapler which is not shown for ease of illustration.

The jaw 2000 of the surgical stapler can be configured to support staples 2010 which can be arranged in any suitable configuration. In this example, the staples 2010 are arranged in rows and create a staple line when deployed to engage tissue. However, it should be appreciated that the staples 2010 may be arranged in a circular or any other configuration, as embodiments are not limited in this respect.

As shown in FIG. 17A, the jaw 2000 serving as a cartridge assembly can be associated with an adjunct material 2012, also referred to interchangeably herein as a tissue reinforcement construct. The adjunct material 2012 can be removably retained on the cartridge body 2006 so as to be positioned over the staples 2010 in any suitable manner. In some embodiments, the cartridge body 2006 can be preloaded with an adjunct material such as the material 2012. In other embodiments, the adjunct material 2012 can be positioned on the cartridge 2006 (e.g., by a surgeon or other medical professional) prior to a surgical procedure.

The adjunct material 2012 can have a configuration such that at least one of peripheral edge portions 2014A and 2014B has a cross section that is larger than a cross-section of a central portion 2016 the adjunct material 2012. The central portion 2016 of the adjunct material 2012 can be defined as a portion that is closer to a longitudinal axis of the cartridge body 2006 than the peripheral edges of the cartridge body. The central portion 2016 and the peripheral edge portions 2014A and 2014B can have any suitable widths. Moreover, the peripheral edge portions 2014A and 2014B can have the same or different widths.

In should be appreciated that the tissue reinforcement construct in accordance with some embodiments can be advantageously used to reinforce a staple line created by the surgical stapler with improved quality relative to existing approaches. For example, in some embodiments, the tissue reinforcement construct can be used to reinforce the staple line 270 degrees around its perimeter. In particular, referring to FIG. 17A, the adjunct material 2012 can be configured such that the peripheral edge portions 2014A and 2014B and a distal portion 2015 have properties such that the staple line created by the staples 2010 can be reinforced. For example, the larger cross-section of the peripheral edge portions 2014A and 2014B makes the adjunct material able to reduce or prevent damage to tissue—e.g., to sensitive tissue in thoracic cavity. Further, in some embodiments, the peripheral edge portions 2014A and 2014B and the distal portion 2015 can be more flexible or stretchable than the central portion 2016 of the adjunct material 2012, which can further help to compress tissue such as the lung parenchyma as it is reinflated after surgery. Additionally or alternatively, in some embodiments, some or all of the peripheral edge portions 2014A and 2014B and the distal portion 2015 can degrade at a faster rate than the central portion 2016, which can lead to a faster rate of release of the inner material of the adjunct material 2012 encompassed within those portions. In this way, tissue in the area around the staple line can be reinforced in an atraumatic way almost immediately after the tissue is penetrated by the staples and/or a knife.

It should be appreciated that the adjunct material 2012 can have any other features that facilitate its use with the surgical stapler. For example, in some cases, the adjunct material 2012 can have cut-out tabs that can be pressed or slid into a knife slot or cartridge of the surgical stapler. When the knife cuts down in the middle of the adjunct material, the tabs are cut out and separated from the stapler.

Figure 17B:
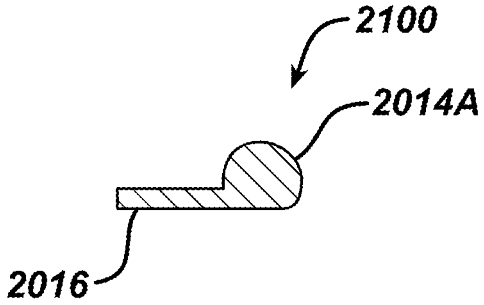
FIG. 17B is a cross-sectional view of a portion of the adjunct material of FIG. 17A, in accordance with some embodiments.

FIG. 17B illustrates an enlarged view 2100 of a cross section 2018 of a portion of the adjunct material 2012 of FIG. 17A. As shown in FIG. 17B, a peripheral edge, such as, for example, the peripheral edge 2014A, may have a larger cross sectional dimension than that of the central portion 2016. The larger cross sectional thickness of the edge portion allows to better seal the areas around the holes created by the staples and prevent tissue tearing. As shown in FIG. 17A, the adjunct material 2012 can be releasably positioned on the cartridge body 2006 so that one or both of the peripheral edge portions 2014A and 2014B extend beyond the cartridge body 2006. This can further improve the way in which the adjunct material 2012, when in an unconstrained configuration upon exposure to moisture, expands and provides effective sealing of a staple line created by the surgical stapler against air or fluid leakage and prevents tearing of the tissue near the staple line.

Figure 18:
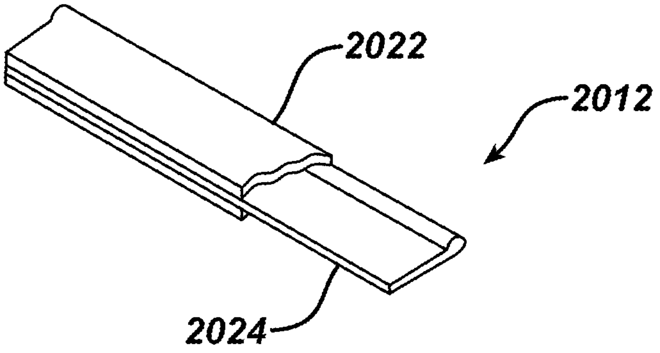
FIG. 18 is a perspective, partially cut-away view of the adjunct material, in accordance with some embodiments.

In some embodiments, the adjunct material 2012 may comprise an outer material that encompasses an inner material maintained within the outer material in a constrained configuration. FIG. 18 shows by way of example that the adjunct material 2012 can comprise a first, outer material 2022 and a second, inner material 2024. The first material 2022 may be a suitable dissolvable and/or absorbable material. The second material 2024 may be a suitable hydrophilic, swellable material. The properties of the first and second material may be uniform throughout or may vary. For example, the first material 2022 may be selectively dissolvable and/or absorbable. Similarly, different portions of the second material 2024 can have different hydrophilicity. For example, in some cases, peripheral edge portions of the second material 2024 can be more hydrophilic than a central portion of the second material 2024.

The first material 2022 may envelop the second material 2024 and, prior to delivering staples (e.g., staples 2010 in FIG. 17A) to the tissue, serve as a moisture barrier. The first material 2022 may be at least partially stretchable or may have any other properties that can be selected based on a clinical application of the adjunct material. For example, in some embodiments, the first material 2022 may be at least partially brittle.

The first material 2022 can prevent exposure of the second material 2024 to moisture for a certain time period—e.g., until the adjunct material 2012 is delivered to the surgical site in the patient's body. When the staples are deployed and the adjunct material 2012 is thus pierced or otherwise penetrated, the second material 2024 begins to swell upon exposure to moisture that passes to the second material 2024 through punctures in the first material 2022. Additionally or alternatively, the first material 2022 can be cut by a knife of the surgical stapler upon its deployment. Furthermore, in some embodiments, the properties of the first material 2022 may be such that the material can crack or otherwise lose its integrity due to compression when it is pressed between the cartridge and anvil of the surgical stapler. For example, if the first material 2022 is brittle, it can be broken by compression.

As discussed above, the first and second materials can be made from a number of suitable biologic materials and/or synthetic materials.

In some embodiments, the first and second material may be selected such that the first material is less hydrophilic than the second material. The same materials (e.g., polymers) may be used to manufacture the first and second materials, but the molecular weight of the source materials may be adjusted differently to produce materials suitable for the first material and materials suitable for the second material. The molecular weight of the polymers can be altered so that to obtain materials having desired degradation properties, as discussed above. For example, mixtures of PGA (Polyglycolic acid and various forms thereof, marketed under the trademarks Vicryl® and/or Neoveil®), and PLA or PLLA (Polylactic acid) can absorb at a relatively fast rate. Similarly, polyhydroxyalkanoate (PHA) can dissolve quickly and the materials made from PHA can begin to degrade within 20 to 30 minutes after attachment to tissue via contact with heat and/or water.

The degradation rates of the first and second material may be selected based on the desired clinical application—e.g., based on a type of treated tissue and/or an amount of time that the adjunct material is desired to remain at the surgical site. For example, a first material for an adjunct material intended to be used in lung surgeries may have a slower degradation rate than that of a first material for the adjunct material to be used to staple vessels. It should be appreciated, however, that embodiments are not limited to materials having any specific degradation rates or any other properties.

Figure 19:
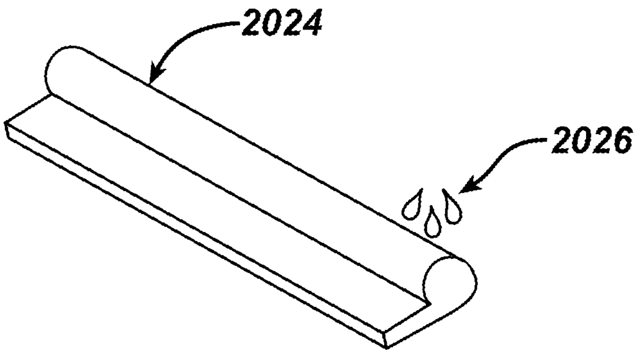
FIG. 19 is a perspective view of an interior hydrophilic, swellable material included in the adjunct material, in accordance with some embodiments.

FIG. 19 illustrates the second material 2024 that can be maintained within the first material 2022 in a constrained configuration—e.g., in a compressed or otherwise constrained configuration. In some embodiments, the second material 2024 can be a hydrophilic foam. The second material 2024 may comprise any suitable material(s) and, in some embodiments, may include one or more therapeutic agents, such as, for example, drugs, promoters of healing, antibacterial agent(s), and antimicrobial agent(s). The therapeutic agent can be configured to be released over time to aid the tissue in healing, for example. In embodiments where more than one therapeutic agent is employed, different therapeutic agents can be configured to release at different rates.

Upon exposure to moisture schematically shown in FIG. 19 as moisture 2026, the second material 2024 can absorb moisture and thus swell and expand. Additionally, if the second material 2024 includes one or more therapeutic substance(s), these substances can begin to elute once the second material 2024 is exposed to moisture. The moisture 2026 can be blood, other bodily fluid, or any other liquid. The adjunct material 2012 can be manufactured such that one or more portions of the second material 2024, can, upon exposure to moisture, expand to transition to a preconfigured shape. The shape of the second material 2024 prior to and after exposure to moisture can be selected so as to provide a good quality seal around the punctures in the tissue created by the staples and provide reinforcement to the staple line against the tissue to prevent tears in the tissue or pulling of the staples through the tissue. For example, as illustrated in FIG. 19, the second material 2024 can have a shape such that its peripheral edges have a larger cross-section than its central portion.

Although FIGS. 17A-19 illustrate the adjunct material 2012 having a shape such that the peripheral edges portions have a larger cross-section than that of the central portion of the adjunct material, it should be appreciated that the adjunct material 2012 can have any suitable shape, as embodiments are not limited in this respect. For example, the adjunct material can have a uniform thickness throughout, or the thickness of the adjunct material can vary in any suitable manner. Regardless of the shape and size of the adjunct material, in some embodiments, the adjunct material can be configured such that one or more portions of the first material are selectively dissolvable and/or selectively absorbable by the patient's body. Furthermore, one or more portions of the second material can be selectively swellable.

Figure 20:
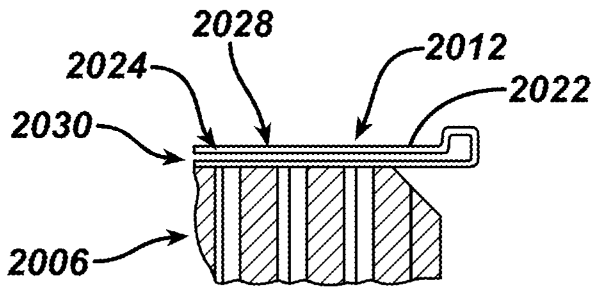
FIG. 20 is a perspective view of the adjunct material before penetration by surgical staples, in accordance with some embodiments.

FIG. 20 is a side view of the adjunct material 2012 removably attached to the cartridge body 2006, prior to deployment of staples supported by the cartridge body 2006. The first material 2022 of adjunct material 2012 comprises a top layer 2028 and a bottom layer 2030, with the second material 2024 sealably enclosed therebetween. As illustrated, a peripheral edge portion of the adjunct material 2012 extends beyond the cartridge body 2006. Such disposition of the adjunct material 2012 with respect to the cartridge body 2006 enhances tissue reinforcement and offers improved resistance to air and fluid leaks around staple holes.

In some embodiments, adjunct materials as described herein may be used in a surgical stapling device that is employed in lung surgery, such as in surgery to treat lung cancer, lung volume reduction surgery, or any other type of surgery. Prior to such surgery, the lung is deflated, and then reinflated to its normal volume after the required procedure is completed. A common complication after such a surgery is that air or fluid can leak though the punctures or holes created by the staples. Moreover, as the lung is being reinflated and the tissue stretches, holes can increase in size (through stretching) or tears can occur in the tissue areas around the staple holes. Accordingly, the described adjunct material can be used to reinforce the tissue around the staple holes and compress the tissue as the lung stretches to assume its normal volume. It should be appreciated, however, that the adjunct material can also be used to seal punctures created by surgical staplers used to secure any other type of tissue, such as, gastrointestinal tissue and vessels (e.g., intestine, stomach and esophagus).

Additionally, in some embodiments, an adjunct material can comprise one or more therapeutic substances, or agents, that can be eluted when the staples are deployed to help healing the tissue at the treatment site, or to prevent or combat infection. The therapeutic substances can be released at different rates to provide the desired action at the treatment site.

Figure 21A:
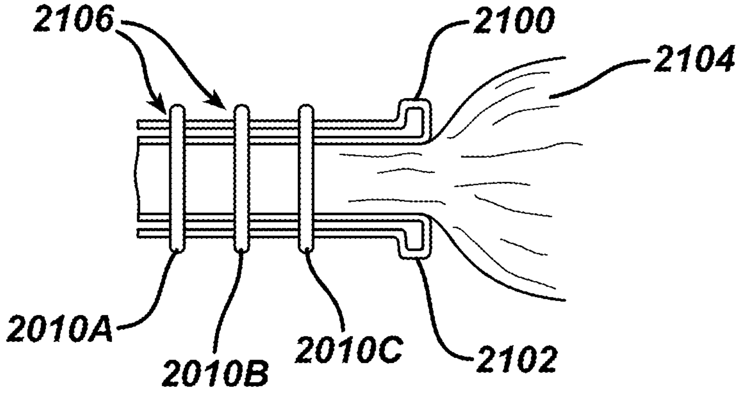
FIG. 21A is a side view of tissue and adjunct materials retained to both the cartridge assembly and anvil of a surgical stapler, after penetration by the surgical staples, in accordance with some embodiments.
Figure 21B:
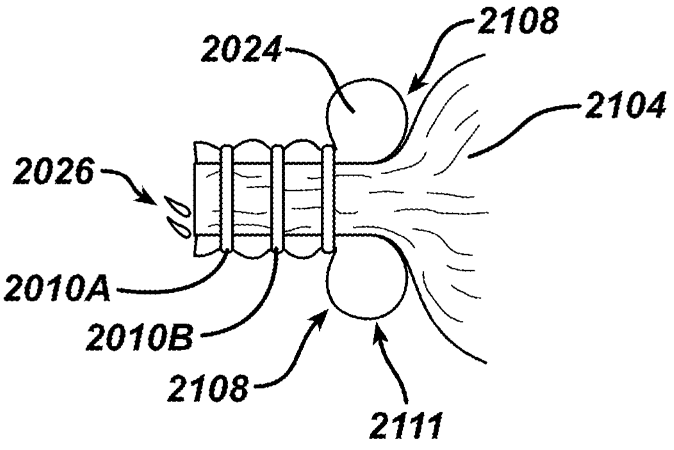
FIG. 21B is another side view of tissue and adjunct materials retained to both the cartridge assembly and anvil of a surgical stapler, after penetration by the surgical staples, in accordance with some embodiments.

In some embodiments, either or both of the cartridge and anvil of the end effector of a surgical stapler can have removably attached thereto an adjunct material such as, for example, the adjunct material 2012. Accordingly, FIGS. 21A and 21B show that two adjunct materials 2100 and 2102 can be used with the surgical stapler to reinforce tissue at a treatment site. When the staples (e.g., staples 2010A-2010C in FIGS. 21A and 21B) are deployed to engage tissue 2104, each of them can create a corresponding puncture in the adjunct material. FIGS. 21A and 21B illustrate by way of example punctures 2106 in the adjunct material 2100. It should be appreciated, however, that the adjunct material 2102 is similarly punctured by the staples 2010A-2010C. In addition, it should be appreciated that only three staples 2010A-2010C are shown for the purpose of illustration only, as embodiments are not limited to any specific number of staples that can be seated in the cartridge body.

The staples deployed to engage the tissue can remain with the tissue until they are removed using an instrument, absorbed by the patient's body or otherwise removed from the treatment site. The adjunct material is maintained at the treatment site by the staples for a certain period of time which can depend on a number of factors—e.g., a period during which the staple holes are expected to heal, a time required for one or more portions of the adjunct materials to disintegrate, and any other suitable factors. Furthermore, one or both of the first and second materials of the adjunct material can be dissolvable and/or (bio)absorbable materials that are gradually absorbed or eliminated in other ways from the patient's body.

FIG. 21A shows the staples 2010A-2010C retaining the adjunct materials 2100 and 2102 at the treatment site of the engaged tissue 2104 at a period of time shortly after the staples are deployed. Because the staples 2010A-2010C penetrate the adjunct materials 2100 and 2102, the integrity of the first layer of the adjunct materials is disturbed, and moisture can pass to activate the second material 2024 encompassed within the first material 2022.

In some embodiments, as shown in FIG. 21B, after a certain time period (which can be of any suitable duration), tissue 2104 begins to expand—e.g., lung parenchyma expands to eventually reach its normal volume, after a surgery was performed on a collapsed lung. At the same time, the second material 2024, which can be hydrophilic, begins to swell upon contact with moisture. As the tissue 2104 expands, the second material 2024 can swell gradually, to transition to a large radius (denoted by way of example using reference numeral 2108 in FIG. 21B) at peripheral edges portions 2109 and 2111 of the adjunct materials 2100 and 2102, respectively.

The first material 2022 encompassing peripheral edge and distal portions of the second material 2024 can stretch to accommodate the expanding volume of the second material 2024. Further, one or more portions of the first material 2022 can be dissolvable and/or absorbable so that the first material 2022 gradually disintegrates as the second material 2024 swells and expands from its constrained form to a predefined shape. In particular, in the embodiment of FIG. 21B, the portions of the first material 2022 at the peripheral edge portions 2109 and 2111 can be configured to dissolve at a faster rate than portions of the first material encompassing a central portion of the second material 2024. Additionally or alternatively, the portions of the first material 2022 at the peripheral edge portions 2109 and 2111 can be configured to absorb at a faster rate than portions of the first material encompassing the central portion of the second material 2024. The described configuration of the first material, where the staple holes in the tissue are sealed and the tissue area surrounding a large portion of the staple line is compressed by the swollen hydrophilic material allows reinforcing the tissue in an effective, atraumatic manner. In this way, the sensitive lung tissue can be sealed so as to prevent bleeding, tearing, and/or leakage of the treated tissue. The ability to create an airtight seal while allowing the tissue to safely stretch around the staple line (e.g., as the lung is reinflated) is particularly useful because the success of the patient's recovery is largely based on how fast the tissue at the surgical site can heal.

As discussed above, in some embodiments, the first, outer material of the adjunct material described herein can have properties that are not uniform throughout. For example, as also discussed above the first material may be selectively dissolvable and/or selectively absorbable. In some embodiments, one or more portions of the first material can be adapted to dissolve at a faster rate than other portions of the first material. Additionally or alternatively, one or more portions of the first material can be adapted to absorb at a faster rate than other portions of the first material. The portions of the first material that are adapted to dissolve and/or absorb at a faster rate can be, for example, peripheral edge portions of the first material, or any other portions.

FIG. 22A illustrates an example of a first material 2201 of an adjunct material 2200 that has portions 2202 adapted to dissolve and/or absorb at a faster rate than portions 2204 of the first material 2200. In this example, the adjunct material 2200 has a uniform, or approximately uniform, thickness throughout. However, it should be appreciated that the thickness of the adjunct material can vary from one portion to another. It should also be appreciated that the alternating portions 2202 and 2204 are shown by way of example only, as the first material can be partitioned into the portions having different dissolution rates and/or portions having different absorption rates in any suitable manner. For example, as mentioned above, the portions of the first material encompassing the peripheral edge portions of the second material can be adapted to dissolve at a faster rate than portions of the first material encompassing the central portions of the second material.

Furthermore, the portions of the first material encompassing the peripheral edge portions of the second material can be configured to absorb at a faster rate than portions of the first material encompassing the central portions of the second material. Additionally, the portions 2202 and 2204 can have different widths, as embodiments as not limited in this respect. By varying the number, length, width and other properties (e.g., materials) of the portions of the first material configured to dissolve and/or absorb at different rates, the second material can be configured to expand at different rates. Different materials can be selected for the first and second materials to obtain desired degradation rates. Depending upon the desired clinical application, different rates at which the second material swells and expands can be controlled to distribute load around the staple line and decrease the possibility of tissue tearing. Additionally, a time during which the adjunct material remains at the treatment site can be adjusted by varying properties of the first and second materials.

FIG. 22B shows an enlarged cross-sectional view of a portion 2208 of the adjunct material 2200 of FIG. 22A. The first material 2201 of the adjunct material 2200 encloses the second material 2206 which may be a hydrophilic foam comprising any suitable material. Similar to FIG. 22A, FIG. 22B also demonstrates that the first material 2201 can comprise portions 2202 configured to dissolve and/or absorb at a faster rate than portions 2204. It should be appreciated that FIG. 22B shows that portions 2202 located on different sides of the second materials 2206 (e.g., portions 2202A and 2202B) are shown to be aligned with each other by way of example only, as embodiments are not limited in this respect.

Figure 23:
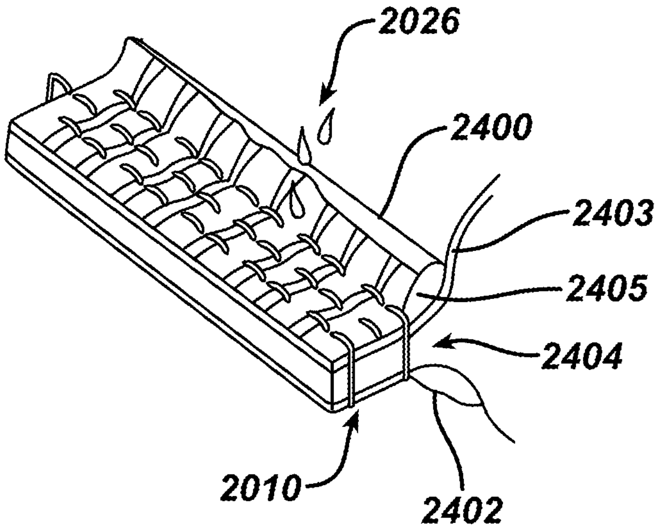
FIG. 23 is a perspective view of the adjunct material illustrating a peripheral edge portion of the adjunct material after penetration by the surgical staples, in accordance with some embodiments.

FIG. 23 illustrates an example in accordance with some embodiments where both a cartridge and anvil side of the surgical stapler can have an adjunct material removably retained thereon. Accordingly, in this example, adjunct materials 2400 and 2402 (e.g., adjunct materials 2200 or any other suitable adjunct materials) are employed to seal punctures in tissue 2404 created by the staples 2010. As shown, when the adjunct materials 2400 and 2402 are pierced by the staples 2010, moisture 2026 from the surrounding environment (e.g., blood, other bodily fluid, water, medication, etc.) passes through the staple holes (e.g., a hole 2408 in FIG. 24) to the inner hydrophilic material (e.g., the second material 2206 of FIGS. 22A and 22B) maintained within an outer layer of the adjunct material.

FIG. 23 also shows that peripheral edge portions of the adjunct materials which, prior to deployment of the staples, extend beyond the cartridge body and/or anvil, can transition to a large radius which may reinforce the tissue 2404. In particular, a peripheral edge portion 2403 of the adjunct material 2400 can transition to a large radius 2405. For example, the portion 2403 can transition from a radius roughly equal to half the thickness of the adjunct (about 0.025 to 1.0 mm) to a radius up to about 5 times the initial size of the feature. However, it should be appreciated that the adjunct material described herein can have any suitable dimensions and, when in an unconstrained form, can transition to a radius of any suitable size, as embodiments are not limited in this respect.

Additionally, a portion of a first material of the adjunct material 2400 (e.g., the first material 2201 of FIGS. 22A and 22B) at the peripheral edge portion 2403 can be such that it dissolves and/or absorbs at a faster rate than other portions of the first material. In this way, the peripheral edge portion 2403 of the adjunct material can disintegrate faster than other areas of the first material, thus allowing the second material encompassed within that portion to swell and expand at a faster rate than the central portion of the second material. As discussed above, the adjunct materials can expand to transition to a predetermined shape, which can be selected based on a clinical application, type of wound to be sealed, and any other factors.

Figure 24:
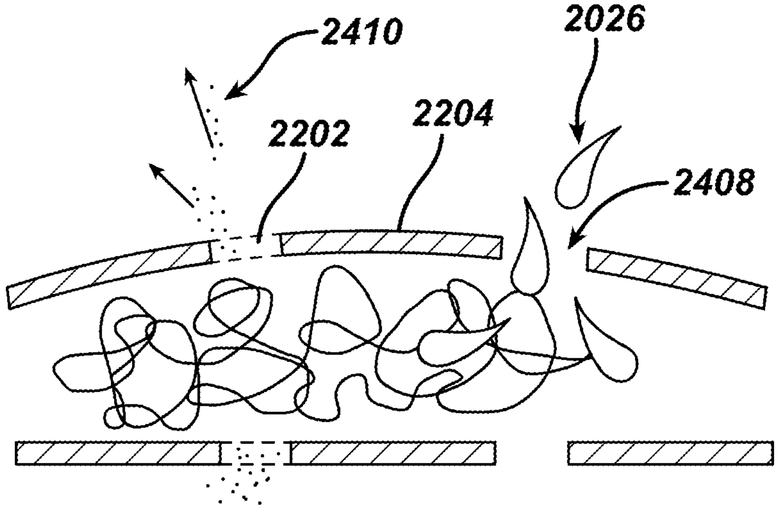
FIG. 24 is a perspective view of the adjunct material of FIG. 23, in accordance with some embodiments.

Additionally, because the outer layer of the adjunct material, such as, for example, the first material 2201, can be at least partially hydrophilic and/or absorbable, one or more portions of this layer, which may or may not be pierced by a staple, can begin to disintegrate as indicated by reference numeral 2410, as schematically shown in FIG. 24 upon exposure to moisture 2026.

The adjunct material described herein may comprise a first material, which is a material encompassing a second material, that can have various properties. For example, as discussed above, the first material can have portions that dissolve at different rates, portions that absorb at different rates, portions of varying widths, etc. The first and second materials can comprise different materials.

Figure 25:
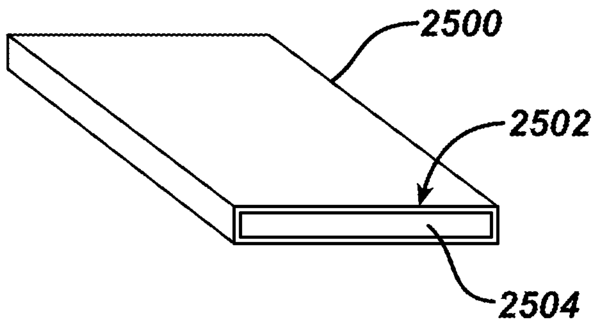
FIG. 25 is a perspective view of an adjunct material having a uniform thickness, in accordance with some embodiments.

An adjunct material 2500 shown in FIG. 25 may have a thickness that is the same or substantially the same along a cross-section of the adjunct material. In this example, a first (outer) material 2502 of the adjunct material 2500 may be brittle. It should be appreciated, however, that the adjunct material in accordance with some embodiments having any suitable shape can be brittle.

The first material 2502 can encompass a second material 2504 which may be a hydrophilic foam made of any suitable material. Additionally, in some embodiments, the second material 2504 may comprise one or more therapeutic substances. The non-limiting examples of the therapeutic substance include fibrin, thrombin, antibiotics, antimicrobial, and antibacterial agents. Suitable agents can include, but are not limited to, triclosan, and silver and copper ions and nanoparticles. It should be appreciated that any number of any suitable therapeutic substances can be included with the second material 2504 and can be eluted with the second material 2504 is exposed to moisture and/or heat in the patient's body.

In some embodiments, tissue is engaged between a cartridge assembly and an anvil of a surgical stapler at a treatment site, wherein at least one of the cartridge assembly and anvil has an adjunct material removably retained thereon. The surgical stapler can then be actuated to eject staples from the cartridge assembly through the adjunct material and into the tissue. The adjunct material can help to reduce impact and trauma from the stapling, distribute stress load on the tissue near the staple line—e.g., as the tissue such as lung parenchyma is stretched after the surgery to its normal volume. It should be appreciated, however, that the adjunct material described herein can be employed in any type of surgery, and embodiments are not particularly limited to lung surgeries.

Figure 26:
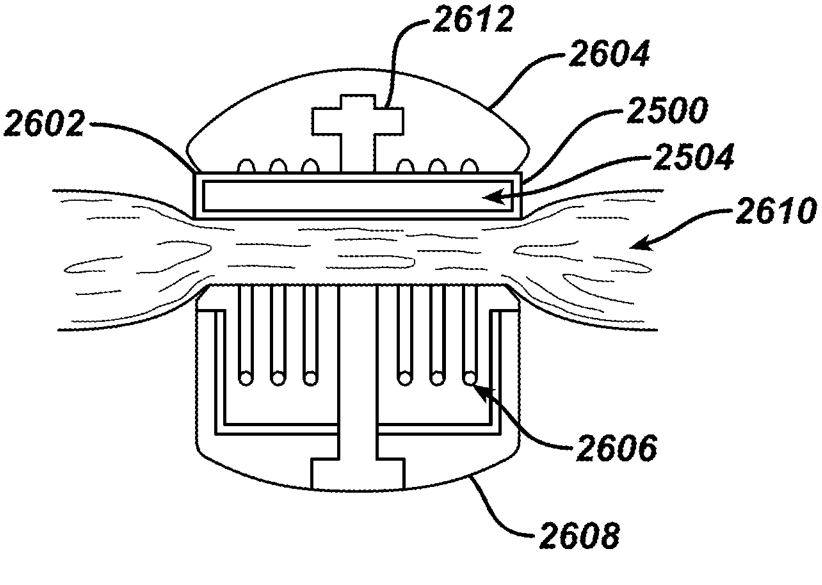
FIG. 26 is a cross-sectional view of tissue and an anvil of a surgical stapler having an adjunct material retained thereon, before penetration of the tissue by surgical staples, in accordance with some embodiments.

In the example illustrated in FIG. 26, an adjunct material 2500 can be positioned on a tissue facing side 2602 of an anvil 2604 of a surgical stapler. When staples 2606 supported by a cartridge body 2608 (which may be similar to the cartridge body 2006 in FIG. 16) are deployed to engage tissue 2610, the first material 2502 of the adjunct material 2500 can fracture so as to expose the second material 2504 to moisture. Additionally or alternatively, the adjunct material 2500 can fracture by being compressed between the anvil 2604 and the cartridge assembly 2608. Furthermore, in embodiments as shown in this example in which the surgical stapler includes a knife 2612, the knife 2612 can also be used to cut the adjunct material 2500 thus exposing the second material 2504 to moisture. Although adjunct material 2500 is shown in FIG. 26 as being disposed on an anvil 2604 of a surgical stapler, adjunct material 2500 may be placed on one or both tissue facing surfaces of opposed jaws of a surgical stapler.

Figure 27:
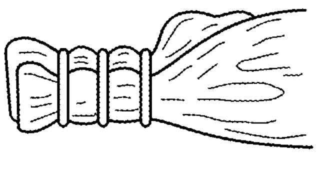
FIG. 27 is a side view of the tissue penetrated by the surgical staples and the adjunct material penetrated and retained by surgical staples, in accordance with some embodiments.

Regardless of the way in which the second material 2504 of the adjunct material 2500 is exposed to moisture, the second material 2504 expands to seal staple holes or prevent them from forming and the therapeutic substance is released to provide the desired effect on the tissue 2610, as shown in FIG. 27.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a dessicant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a dessicant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A staple cartridge assembly for use with a surgical stapler, comprising:

a cartridge body having a plurality of staple cavities configured to seat staples therein; and a tissue reinforcement construct removably attached to the cartridge body and configured to be delivered to tissue by deployment of the staples in the cartridge body, the tissue reinforcement construct comprising a first, dissolvable material encompassing a swellable, hydrophilic second material such that the second material is maintained within the first material in a constrained configuration, wherein the second material has a preconfigured shape such that, in an unconstrained configuration, the second material is adapted to expand to the preconfigured shape in which a peripheral edge portion of the second material has a thickness that is greater than a central portion of the second material.

2. The assembly of claim 1, wherein at least a portion of the first material is less hydrophilic than the second material.

3. The assembly of claim 1, wherein the first material is brittle.

4. The assembly of claim 1, wherein the second material comprises a foam material.

5. The assembly of claim 1, wherein the first material is selectively dissolvable such that portions of the first material encompassing the peripheral edge portions of the second material are configured to dissolve at a faster rate than portions of the first material encompassing the central portion of the second material.

6. The assembly of claim 1, wherein the first material comprises at least one first portion and at least one second portion, and the first material is selectively dissolvable such that the at least one first portion is configured to dissolve at a faster rate than the at least one second portion.

7. The assembly of claim 1, wherein the first material is selectively absorbable such that portions of the first material encompassing the peripheral edge portions of the second material are configured to absorb at a faster rate than portions of the first material encompassing the central portion of the second material.

8. The assembly of claim 1, wherein the first material comprises at least one first portion and at least one second portion, and the first material is selectively absorbable such that the at least one first portion is configured to absorb at a faster rate than the at least one second portion.

9. The assembly of claim 1, wherein the first material is selected from the group consisting of polydioxanon, polyhydroxyalkanoate (PHA), polyglycerol sebacate (PGS), polyglycolic acid, polylactic acid (PLA), poliglecaprone 25, polyglactin 910, poly glyconate, polyglycolide-(PGA), polyglycolide-trimethylene carbonate (PGA/TMC), polyhydroxybutyrate (PHB), poly(vinyl pyrrolidone) (PVP), poly (vinyl alcohol) (PVA), absorbable polyurethanes, a blend thereof, and a copolymer thereof.

10. The assembly of claim 1, wherein the second material is selected from the group consisting of polydioxanon, polyhydroxyalkanoate (PHA), Polyglycerol sebacate (PGS), polyglycolic acid, polylactic acid (PLA), poliglecaprone 25, polyglactin 910, poly glyconate, polyglycolide (PGA), polyglycolide-trimethylene carbonate (PGA/TMC), polyhydroxybutyrate (PHB), poly(vinyl pyrrolidone) (PVP), poly (vinyl alcohol) (PVA), absorbable polyurethanes, a blend thereof, and a copolymer thereof.

11. The assembly of claim 1, further comprising at least one therapeutic agent incorporated into at least one of the first material and the second material, the at least one therapeutic agent being effective to be released upon one of absorption of the first material and expansion of the second material upon exposure to moisture.

12. The assembly of claim 1, wherein the tissue reinforcement construct is shaped such that a cross-section of the peripheral edge portion of the tissue reinforcement construct is larger than a cross-section of the central portion of the tissue reinforcement construct, the central portion being closer to a longitudinal axis of the tissue reinforcement construct than the peripheral edge portion.

13. The assembly of claim 12, wherein the preconfigured shape is such that the central portion of the second material transitions to a large radius at the peripheral edge.

14. A staple cartridge assembly for use with a surgical stapler, comprising:

a cartridge body having a plurality of staple cavities configured to seat staples therein; and an adjunct material releasably retained on the cartridge body and configured to be delivered to tissue by deployment of the staples in the cartridge body, the adjunct material comprising a first material encompassing a second material, wherein:

the adjunct material is configured to be penetrated by the staples being delivered to the tissue such that the first material is penetrated so as to expose the second material to moisture; and the second material is configured to expand to form a seal around at least one staple of the staples inserted therethrough upon the exposure to moisture, wherein the seal is formed such that a peripheral portion of the second material transitions to a large radius than a remainder of the second material.

15. The staple cartridge assembly of claim 14, wherein the adjunct material is positioned on the cartridge body such that at least a portion of the adjunct material extends beyond the cartridge body.

16. A method for joining tissue, comprising:

engaging tissue between a cartridge assembly and an anvil of a surgical stapler at a surgical site, at least one of the cartridge assembly and the anvil having an adjunct material releasably retained thereon, the adjunct material comprising a first material, at least a portion of which is configured to dissolve when exposed to bodily fluid, and a second material constrained within the first material in a constrained form; and actuating the surgical stapler to eject staples from the cartridge into the tissue such that at least one staple from the staples extends through the adjunct material to maintain the material at the surgical site, wherein the second material is configured to transition to a predetermined shape upon dissolution of the first material such that at least a peripheral edge portion of the adjunct material has a thickness greater than a central portion of the adjunct material.

* * * * *